United States Patent [19]
Moore et al.

[11] Patent Number: 5,930,759
[45] Date of Patent: Jul. 27, 1999

[54] METHOD AND SYSTEM FOR PROCESSING HEALTH CARE ELECTRONIC DATA TRANSACTIONS

[75] Inventors: James G. Moore; Wayne E. Jones, both of Houston, Tex.

[73] Assignees: Symbol Technologies, Inc., Holtsville, N.Y.; Optimum, Inc., Houston, Tex.

[21] Appl. No.: 08/641,173

[22] Filed: Apr. 30, 1996

[51] Int. Cl.$^6$ .......................... B42D 15/00; G06F 15/30; G06F 7/00; G06F 159/00
[52] U.S. Cl. ...................... 705/2; 705/3; 705/4; 705/40; 283/117; 283/68; 283/69; 283/78
[58] Field of Search .................................. 705/2, 3, 4, 5

[56] References Cited

U.S. PATENT DOCUMENTS

| | | | |
|---|---|---|---|
| 5,220,501 | 6/1993 | Lawlor et al. | 364/408 |
| 5,301,105 | 4/1994 | Cummings, Jr. | 364/401 |
| 5,319,181 | 6/1994 | Shellhammer et al. | 235/462.09 |
| 5,337,361 | 8/1994 | Wang et al. | 380/51 |
| 5,381,487 | 1/1995 | Shamos | 382/2 |
| 5,399,846 | 3/1995 | Pavlidis et al. | 235/462.1 |
| 5,465,082 | 11/1995 | Chaco | 340/825.54 |
| 5,557,514 | 9/1996 | Seare et al. | 364/401 |
| 5,644,778 | 7/1997 | Burks et al. | 395/800 |
| 5,737,539 | 4/1998 | Edelson et al. | 395/203 |
| 5,748,907 | 5/1998 | Crane | 395/202 |

FOREIGN PATENT DOCUMENTS 0 652 528 A2  5/1995  European Pat. Off. ........ G06F 19/00

OTHER PUBLICATIONS

Doug Picker, Symbol Technologies announces 2–D symbology PDF 417 for new applications, Symbol Technologies News Release, 2 pages, Oct. 2, 1990.

"Jerry Brager identified a need for computers in health care, and now he is making his vision come true", Business for Central New Jersey, v6, n8, s1, p34, Apr. 14, 1993.

Gifford M. Mabe, The electronic highway, Computers in Health Care, v8, n14, p39–40, Dec. 1967.

Itkin et al., "A PDF 417 Primer: A Guide to Understanding Second Generation Bar Codes and Portable Data Files," Symbol Technologies, Inc., Bohemia, New York, (Apr. 1992).

"Screen Phone & Services: The Next Generation Telephone," Philips Home Services, Inc. (1994).

"Philips P100 Screen Phone: The Next Generation Telephone," Philips Home Services,Inc. (1994).

"The Next Logical Step: Financial Services," Philips Home Services, Inc. (1994).

*Primary Examiner*—Allen R. MacDonald
*Assistant Examiner*—Pedro R. Kanof

[57] ABSTRACT

A system or network for assembling, filing and processing health care data transactions and insurance claims made by patients pursuant to health care policies issued to the patients by insurance companies or other carriers for service provided to the patients at health care facilities. The network comprises a multitude of participating patients, a multitude of health care facilities, and a plurality of insurance companies or other carriers. Each of the patients has a personal data file including a set of patient related data encoded in a machine readable format, and each of the health care facilities has a telecommunications unit and a file reader to read the data on the personal data files and to transmit the patient related data to the telecommunications unit at the facility. The network further includes a central claims processing unit connected to the telecommunications units of the health care facilities to receive the electronic claim forms from those facilities and to adjudicate those claims.

29 Claims, 36 Drawing Sheets

| | Name | SSN | DOB | Emp | Plan |
|---|---|---|---|---|---|
| | | | 10/22/60 | 7276 | 5463 |
| | | | 04/20/45 | AJ205 | 7689 |
| | | | 01/29/67 | K254 | 89876 |
| | | | 08/23/60 | 2254 | 098 |
| | | | 05/12/41 | 998G | 7675 |
| | | | 07/14/50 | K254 | 7675 |
| | | | 03/05/52 | 72B5 | 6785G |
| | | | 11/21/45 | 2254 | 7675 |
| | | | 02/15/70 | 998G | 7675 |
| | | | 12/17/73 | 5479 | 98786 |
| | | | 03/25/61 | 72B56 | 98786 |
| | | | 07/07/55 | AJ205 | 98786 |
| | | | 09/02/49 | 998G | 7675 |
| | | | 02/13/65 | 998G | 7675 |
| | | | 01/20/45 | 72B5 | 6785G |
| | | | 02/12/56 | 2254 | 987Y |
| | | | 01/01/65 | 627D | AT5463 |

Provider Information — Dr. Hxxxx Rxxxx  Go Drive Suite 420 Houston, Texas 77077 (31a)

Insurance Co. of US, 10 Your Street, City, ST 77788 (31b)

Scan these Macro Data Codes for:
Eligibility 800-234-5678 (31c)
Encounter Submittal (31d)

31a – Provider Information
31b – Insurance Company Information
31c – Portable Data File for Eligibility Information
31d – Portable Data File Containing information about insurance company, payor, provider, and transmisson data
31e – Portable Data File containing patient information used to complete insurance claim form
31f – Human readable patient information

FIG. 3

Macro Data Code
for
Dental Indemnity and Dental HMO Plans

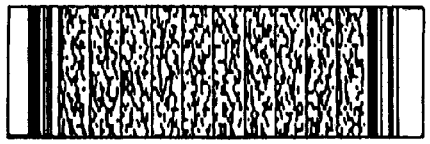

Base Marco Data Code

On-Line Macro Data Codes

Eligibility    Benefits

Section I     Macro Data Code Printer (a)

Section II    Type Plan (b)

Section III   Plan Demographics (ANSI Standard 837)
- Carrier Information (f)
- Employer Information (e)
- Employee/Subscriber Information (d)
- Patient Information Spouse (c)
- Patient Information Child No. 1
- Patient Information Child No. 2
- Patient Information Child No. 3
- Patient Information Child No. 4
- Patient Information Child No. 5
- Patient Information Child No. 6

Section IV    Plan Eligibility (g)*

Section V     Plan Benefits/Dental (h)
              Plan Benefits/Medical

Section VI    On Line Adjudication (i)

Section VII   Transmitting and Receiving Data (j)

Section VIII  Optional Information (k)

Section IX    Human Readable Section (l)

| Patient Name [First, MI, Last] | Plan Dates [mm/dd/yy to mm/dd/yy] Printer___ |
|---|---|
| Patient's SS # [___-__-____] | Payor_____ Type Plan_____ |

FIG. 4

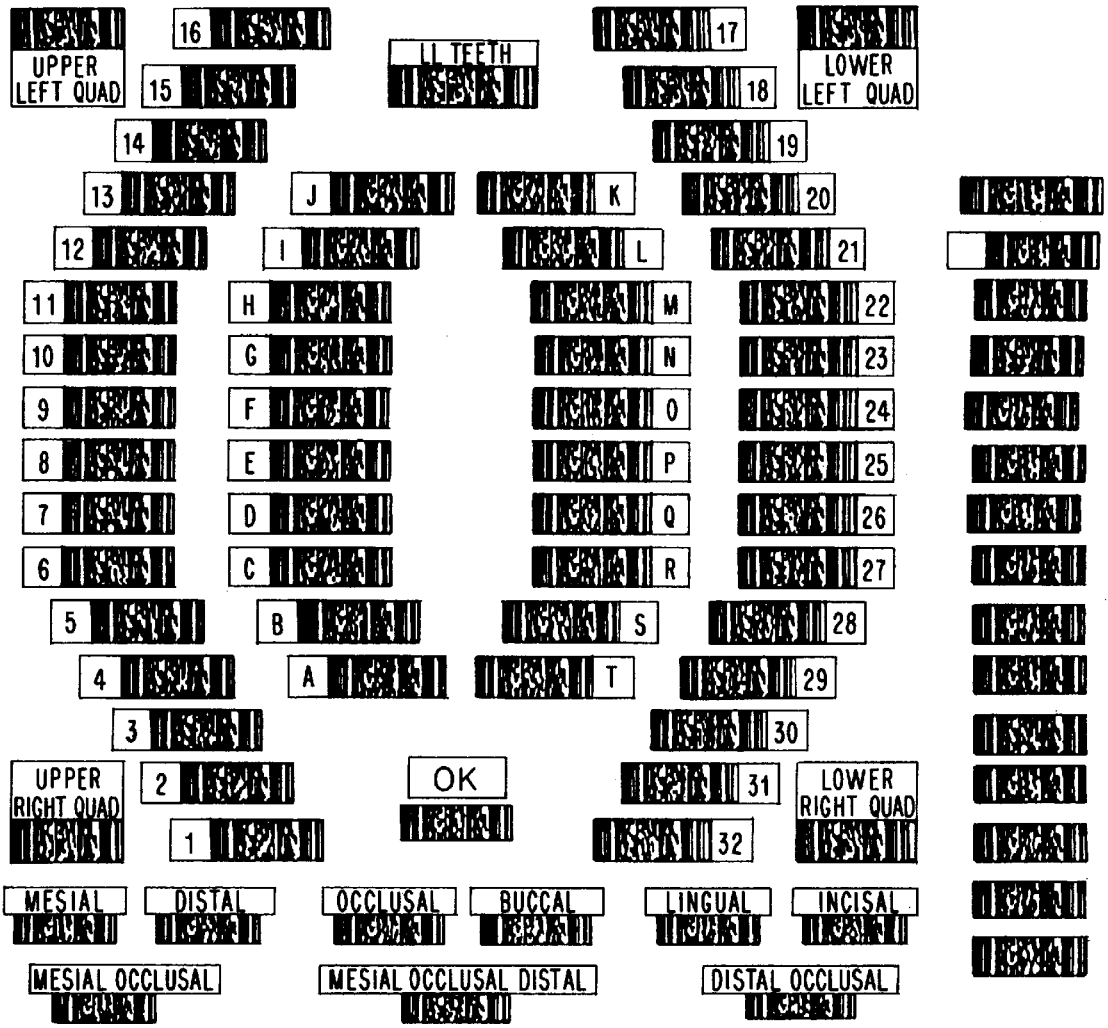
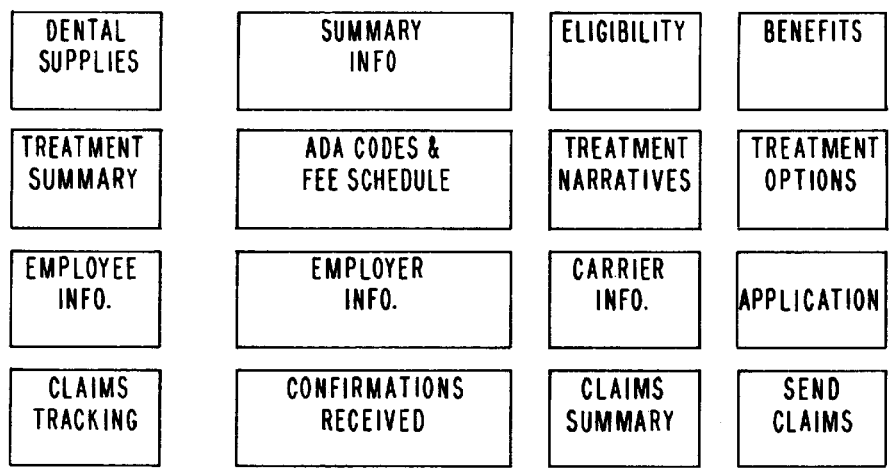
FIG. 8

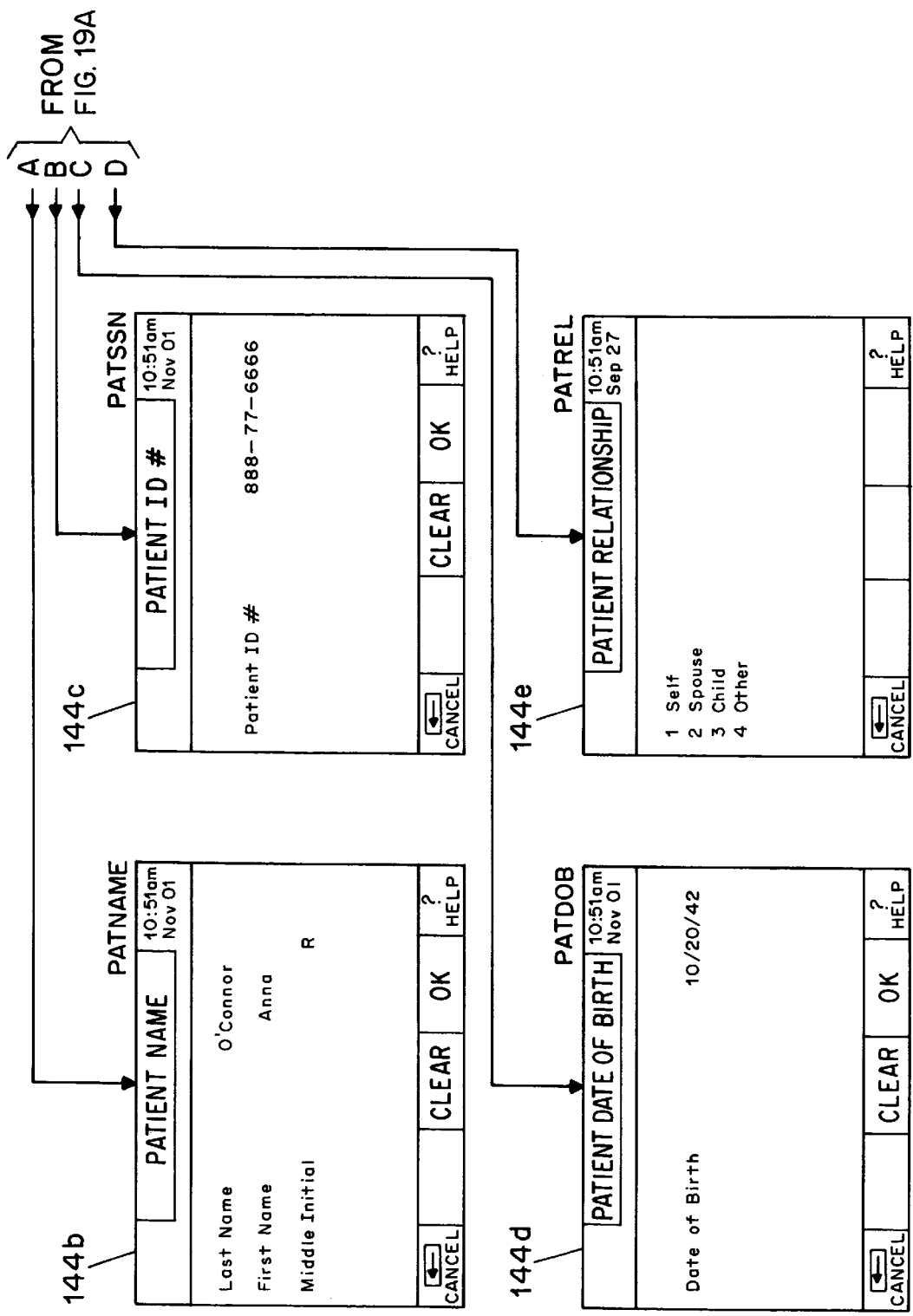

150 →

INSURANCE CLAIM RECEIPT

150a — Date __/__/__

150b {
Claim No._____
Patients Name_____
SSN ___-__-____
}

150c — Treating Dentist_____

150d — | Macro Data Code |

150e {
Treatment Codes____, ____, ____,
____, ____, ____, ____, ____,
____, ____, ____, ____
}

Total Fee $ [_____] — 150f

150g { Remarks_____
_____ }

FIG. 21

METHOD AND SYSTEM FOR PROCESSING HEALTH CARE ELECTRONIC DATA TRANSACTIONS

BACKGROUND OF THE INVENTION

This invention generally relates to a system or network for preparing and processing health care data transactions such as dental or medical insurance claims. More specifically, the present invention relates to such a system or network that is highly automated, very accurate and very simple to use.

The preparation and processing of health care data transactions such as insurance claims, especially medical and dental claims, has become a ubiquitous and aggravating procedure. For example, in 1993, approximately 3.6 billion medical insurance claims were filed, and an additional 387 million dental insurance claims were filed. Of these claims, over 2.3 billion claims were filed using paper claim forms.

In order to file just a single claim using paper forms, typically the patient and health care personnel provide a significant amount of data on one or more forms, and often this is done by hand printing or hand typing that data on the form or forms. For instance, the patient, or personnel at a health care facility, may complete one form, or a part of one form, by printing or typing on that form the patient's name, address and date of birth, information relating to the insurance company and information about the treated condition. Health care personnel then add information to that form, or another form, further describing the treated condition, describing the procedure or service received by the patient, and describing the individual providing that procedure and other related or supplemental information needed to process and adjudicate the claim.

After the appropriate form or forms are completed, they are mailed either to the insurance company or other carrier or to a third party administrator to be processed. In either case, upon receipt, the processor opens the envelope and manually inputs information on the forms into their own computers. Then, after a decision is made as to whether payment for the procedure is appropriate, and if so, the amount of such payment and the proper payee, a check is prepared and mailed to that payee. Additional manual labor may be needed to keep track of the total amount of claims submitted by each patient during a specified period and to keep track of other matters, such as for statistical purposes.

Not only is the preparation and processing of these paper forms time consuming and aggravating, it also adds substantially to the cost of health care. Another disadvantage of the paper forms is that errors are often made when the forms are filled out. For example, with some claims processing systems, up to 30% of the submitted claim forms have some type of error. This high percentage of errors is because, among other reasons, it is very easy to omit necessary information or to make mistakes when putting information on the forms. If data is missing from, or is not correct in, a claim form, then normally the form must be returned to its originator, causing additional work and delays in the processing of the claim.

Semi-automated procedures, using personal computers or other types of conventional computers, to prepare or to help prepare insurance claims or to process other health care data transactions are known. Typically, though, these procedures still require a significant amount of manual work, or require considerable computer operating skills. The requirements of these semi-automated procedures discourage people from using them. As a consequence, most people prefer the more time consuming and less accurate—but more familiar—routine of filling out paper forms by hand.

SUMMARY OF THE INVENTION

An object of this invention is to improve systems for preparing and processing health care data transactions and insurance claims.

Another object of this invention is to provide a method of filing electronic data transactions and insurance claims that does not require the use of a typical personal computer or other type of conventional computer.

A further object of the present invention is to provide a complete, automated data processing system for electronically assembling health care data transactions that is very simple to use, can be used by a computer novice, and that can be effectively implemented without requiring any, or any significant, keyboard operations.

Another object of the present invention is to provide a complete system for preparing and processing health care data transactions and insurance claims without any paper claim forms.

Another object of this invention is to provide a health care insurance card having machine readable data encoded thereon to facilitate electronically preparing, routing and processing health care insurance transactions, claims and other data manipulations.

Still another object of the present invention is to provide a patient roster having machine readable data encoded thereon that can be used by health care facilities to prepare health care insurance encounter forms for any patient on the roster without requiring any manual input of any additional patient related data.

Another object of this invention is to provide personal patient data files having machine readable data encoded thereon and that can be used by a health care facility to prepare a complete health care insurance claim, and to obtain eligibility, policy benefit and other related data at the time and place at which services are provided to the patients. These data files may be in several forms or combinations of forms. For example, individual, portable cards may be made, with each card having the personal patient data file for a respective patient encoded thereon. Alternately, or in combination with the foregoing, individual health care facilities may be given printed patient rosters containing the personal portable data files of patients that have a defined association with the facility.

A further object of the present invention is to provide a health care insurance network in which claims made for services received by an individual may be prepared at the time and at the facility at which the services are provided without requiring that the providing facility have any prior knowledge or information about the individual.

Another object of this invention is to provide a health care network in which any participating person can go to any participating office or facility in the network regardless of whether that office or facility has any prior knowledge or data about the person, and that office or facility, using a unique insurance card issued to the person, can prepare a complete insurance claim for services provided to the person at the time and place at which those services are provided, These and other objectives are attained with a system or network for assembling, filing and processing health care data transactions and insurance claims made by patients pursuant to health care policies issued to the patients by insurance companies or other carriers for service provided to the patients at health care facilities. The network comprises a multitude of participating patients, a multitude of health care facilities, and a plurality of insurance companies or other carriers.

In one embodiment of the network, each of the patients has a respective portable personal data file including a set of patient related data encoded in a machine readable format. Each of the health care facilities has a telecommunications unit, and a file reader to read the data on the personal data files and to transmit the patient related data to the telecommunications unit at the facility. The telecommunications unit includes a control program having (1) a series of prompts, and (2) a claim assembling program to present the prompts in a human understandable format to solicit from an operator the data related to services provided to the patients at the health care facility, and to assemble the patient related data from the personal data files and the service related data from the operator into electronic claim forms. Much of this assembly and data manipulation may be accomplished by scanning, not keyboard response.

The network further includes a central claims processing unit connected to the telecommunications units of the health care facilities to receive the electronic claim forms from those facilities and to check for errors on those claims. The central claims processing unit is also connected to telecommunications units at the insurance companies or other carriers where the adjudication of those claims is accomplished made pursuant to policies issued by the carrier or insurance company.

Preferably, the personal data files are two-dimensional bar codes printed in PDF417 format, and each patient's bar code contains all of the information about the patient that is needed to prepare an electronic claim form. The bar code may contain additional data to help facilitate and expedite the preparation, filing, processing and collecting of the health care claims or to obtain health care information electronically, such as eligibility and policy benefits.

These two dimensional bar codes may be in a variety of forms or combinations of forms. For example, individual portable cards that are the size of standard credit cards may be made, with each card having one patient's bar code printed thereon. Alternatively, or in combination with the foregoing, printed patient rosters containing the bar codes of patients that have defined associations with particular health care facilities may be made and given to those facilities. Also, preferably, each health care facility has the ability to print bar codes on adhesive labels, and these labels can then be attached to other documents such as patient charts.

The highly automated and accurate system disclosed herein in detail captures data and data fields and uses them to file health care insurance claims, inquire electronically about the patient eligibility and policy benefits, electronically checks unprocessed insurance claims, and automatically adds narrative discussions for electronic transmissions.

Further benefits and advantages of the invention will become apparent from a consideration of the following detailed description, given with reference to the accompanying drawings, which specify and show preferred embodiments of the invention.

BRIEF DESCRIPTION OF THE DRAWINGS

FIG. 3 shows a patient roster having personal portable data files for a group of patients.

FIG. 4 is a chart illustrating a personal data file and outlining information that may be contained therein.

FIG. 8 is a chart showing a variety of bar codes that may be used to input information to the telecommunications unit.

FIGS. 10A–10H illustrate additional screens that may be shown as a claim is assembled.

FIG. 21 shows a receipt that is kept by the doctor's office when a health care claim is filed.

DETAILED DESCRIPTION OF THE PREFERRED EMBODIMENTS

Figure 1:
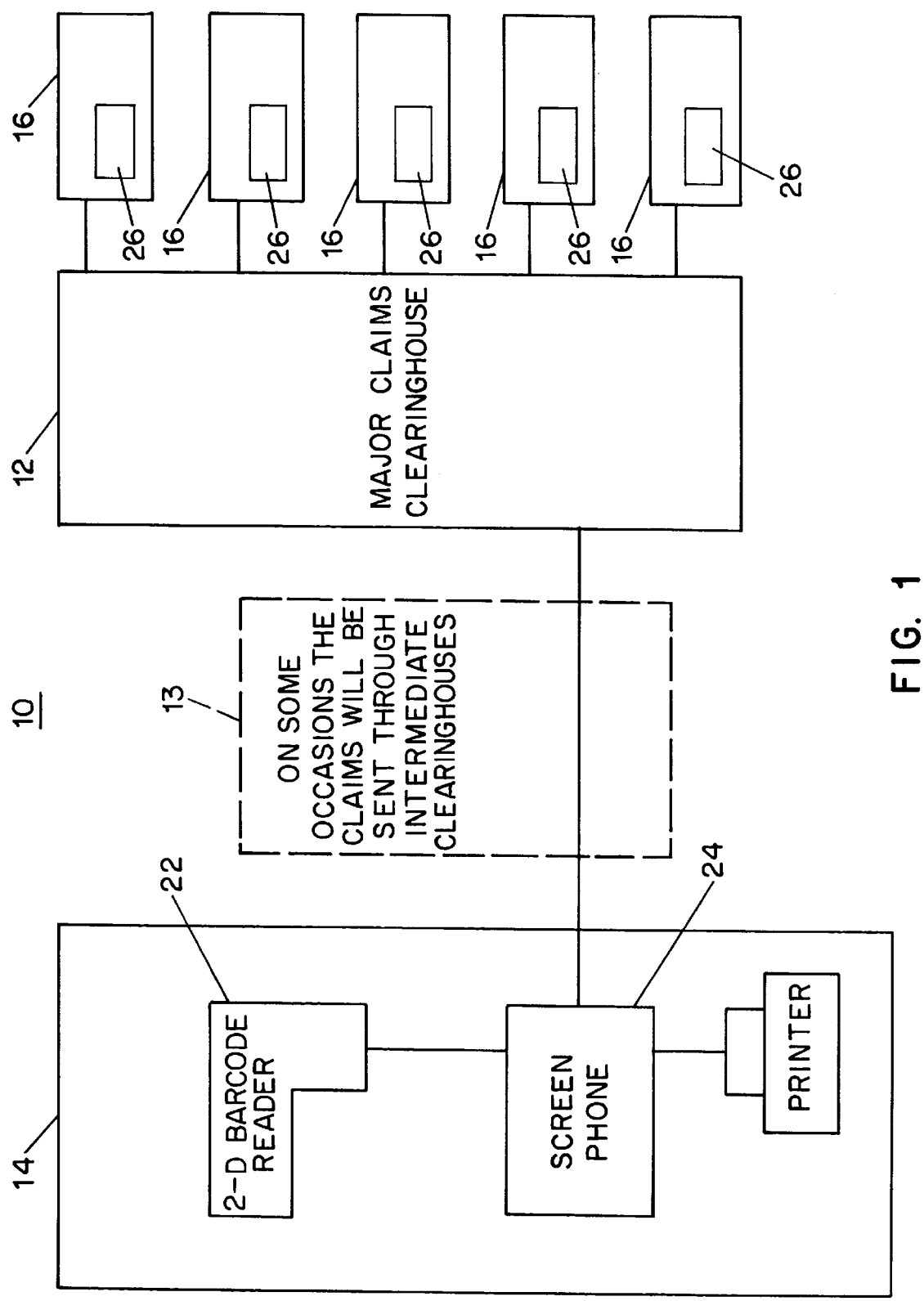
FIG. 1 is a schematic drawing of a network for preparing and processing health insurance claims.

FIG. 1 illustrates network 10 for electronically assembling, filing and processing health care data transactions and insurance claims; and the network includes central claims clearinghouse 12, a multitude of participating health care offices or facilities 14 (only one is shown in FIG. 1), and a plurality of participating payors 16 such as insurance companies or other carriers. More specifically, network 10 is designed to electronically assemble, file and process health care electronic data interchange (referred to herein as EDI) transactions and insurance claims made by patients or participating members for services or treatments provided by health care providers at or in association with health care facilities 14 and made pursuant to insurance policies or coverages issued to those patients by insurance companies or other payors 16.

Figure 2:
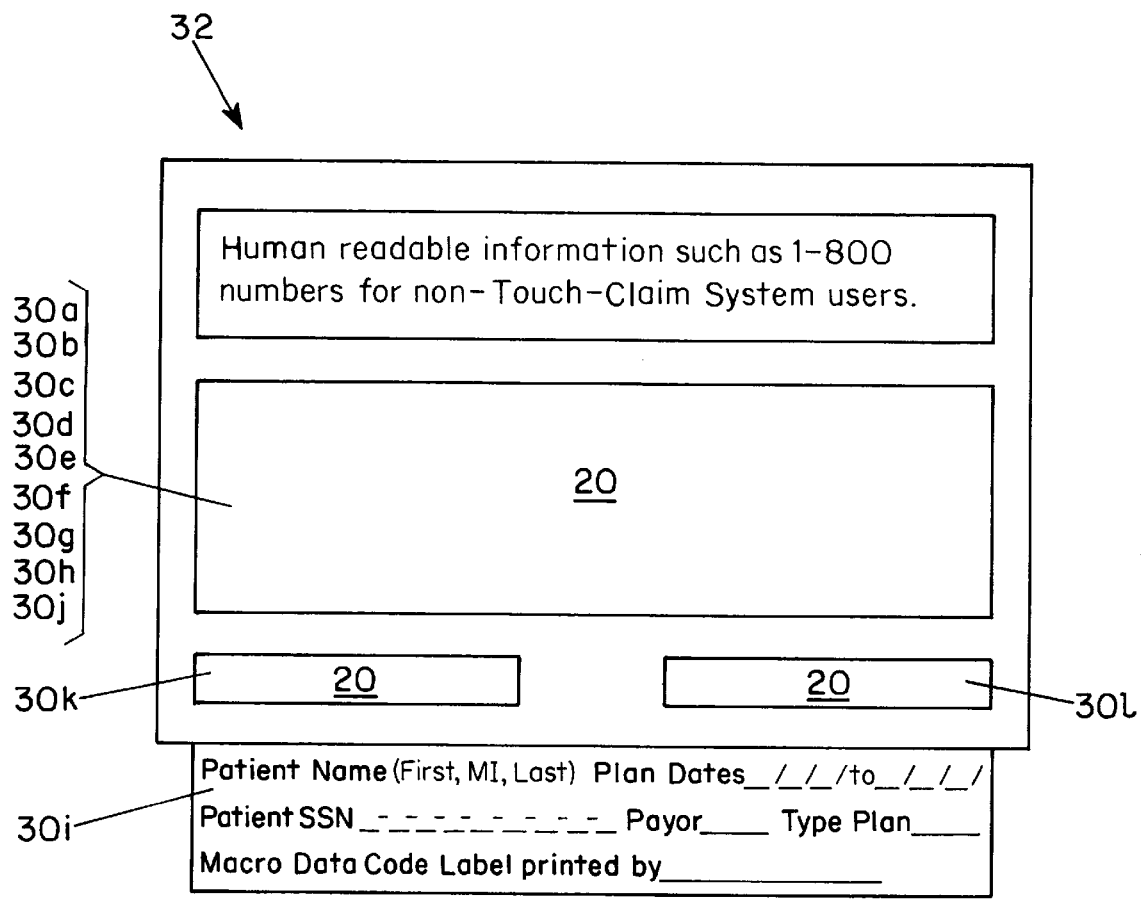
FIG. 2 shows a portable personal data file that may be used in the network of FIG. 1.

With reference to FIGS. 1–3, each participating individual covered in network 10 is provided with a respective personal data file 20, and each participating office or facility 14, is provided with a file reader 22 and a telecommunications unit 24. Also, each participating insurance company or payor 16 has a processing or telecommunications unit 26 for communicating with the central claims clearinghouse 12.

Each patient's personal data file 20 contains information about the patient encoded in a machine readable format. In the operation of network 10, when a patient receives health care at a facility 14, reader 22 is used to read the data on the patient's personal data file and to transmit that patient data to the telecommunications unit 24 at the facility. In a manner more fully discussed below, an operator then inputs to the telecommunications unit additional data related to the treatment received by the patient. The telecommunication unit assembles the patient related data and the treatment related data into a data set referred to as a health care electronic transaction or claim form, and that data set is transmitted to central claims clearinghouse 12.

Generally, clearinghouse 12 serves as an electronic routing system for the claims and checks to determine if the information is complete.

Upon receipt of this electronic claim form, clearinghouse 12 processes that claim or transaction and sends it on to the patient's insurance company or other health care payor to determine various items of information such as eligibility, policy benefits, claim dates, a payment amount and the names of the payor and payee. Processing unit 12 also identifies the insurance company or payor that issued the policy or plan under which the claim is being made. The insurance or other health care payor then determines the appropriate response to the claim. On some occasions the claims will be sent through intermediate clearinghouses 13.

Network 10 is very well suited for use as a complete system for preparing and submitting health care claims made by a large number of patients pursuant to insurance policies or other plans issued by many insurance companies or payors and for services and treatments provided at a large number of facilities. Also, the claims can be completely assembled electronically, without any paper forms, without the need for any highly skilled computer operator, and with a very high degree of accuracy. Moreover, by taking advantage of the unique features and benefits of network 10, this network may be, and preferably is, designed so that the claims may be prepared at the time and place at which the health care services are provided to the patients. The personal portable data files 20 are an important part of the network that helps the network achieve these significant benefits.

As mentioned above, each patient's personal data file 20 contains information about the patient, encoded in a machine readable format, that is used to help prepare the electronic claim form, and preferably each patient's personal data file contains all of the information about the patient that is needed to prepare the electronic claim form. For example, data file 20 may contain encoded personal data such as name, address and social security number, physical data such as age, height, and eye color, information about relatives, insurance policy information, and a personal identification number.

Personal data files 20 may take a variety of specific forms. Preferably, as generally illustrated in FIGS. 2 and 3, the data file is a two-dimensional pattern 30, referred to as a two-dimensional bar code, printed on a carrier. For instance, as shown in FIG. 2, the bar code can be printed on a paper or plastic card 32 that can be readily carried by an individual. Also, with reference to FIG. 3, groups of data files 20 may be printed on patient rosters 34 that are given to the health care facilities. More specifically, a given health care facility may have a group of patients that have a defined relationship or association with that facility; and, for instance, these patients may have designated one to the physicians at that facility as a primary care physician under a health maintenance organization plan. That facility may be provided with a patient roster having printed thereon the bar codes for all the patients having that defined relationship with the facility.

The bar codes 30 can also be printed on stickers or labels that can be attached to some other item or document such as a patient chart, and preferably, each facility 14 has the capability of printing the bar codes 30 on such stickers or labels. For example, if the patient is admitted to a hospital, the bar code can be printed on a sticker that is attached to the patient's hospital chart.

With the above-described arrangement, when a participating individual first visits a specific facility 14, the reader 22 at that facility is used to read the bar code 30 on the patient's personal data file 20 and to transmit the patient related data to the telecommunications unit 24 at the facility. For example, if this data is on a card 32, the individual may take that card to the health care facility. IF the facility already has the bar code on some document, for example on a patient roster 34, the bar code may be read from that other document.

The data on the bar code that is transmitted to the telecommunications unit 24 is stored in an electronic memory area or file area of the telecommunications unit, producing a data file at the facility for the individual. That data may then be used to return policy information, eligibility or benefits or to process a treatment claim, and preferably the data is transmitted to a permanent electronic file at the facility. Subsequent needs for any of this data, either during that first visit or during future visits, may be satisfied, for example, by copying the bar code on a printed label and attaching it to the patient's facility record, eliminating the need to use continuously the data card. Also, printed copies of the personal data in the bar code, or of the bar code itself, may be made and placed on the patient's chart, to be used during treatment of the patient.

The preferred embodiment of bar code 30 illustrated in FIG. 2 has a multitude of sections. With reference to FIGS. 2 and 4, section 30a contains data that is used by a printer to reprint the bar code, and in particular, this section of the bar code contains information relating to the payor, the provider/doctor, the practice management database, the clearing house, and other related information. Section 30b contains data identifying the type of insurance or coverage plan held by the patient. For example, the insurance or coverage may be indemnity, indemnity/HMO switch, Medicare or Medicaid. This section of the bar code may also contain other related data.

Section 30c contains information referred to as plan demographics, and this data may be the same as or similar to the information identified by an insurance industry standard referred to as ANSI standard 837. In particular, this section of the bar code contains information about the patient such as his or her name, the patient's relation to the employee, the patient's sex, and the patient's date of birth. This section of the bar code may also contain information about the employee/subscriber such as his or her name, mailing address, social security number, date of birth, group policy number and dental plan identification number. Preferably, section 30c also has employer information such as its name, group policy number and address, and has carrier information such as its name, identification number, address and electronic address.

Section 30d of the bar code contains data describing the eligibility requirements of the plan. For instance, this bar code section may contain a phone number to which information may be transmitted, may contain a free text area, and may have a database phone number with patient identifier. Section 30e contains information about the plan benefits, particularly its medical and dental benefits. For example, this section of the bar code may have a benefits phone number, the plan dates, the waiting period, copayments, the deductible, and the yearly maximum; and bar code section 30c may have other information referred to as preventive, basic, major, frequency PX, and frequency BWX. Information identifying an initial placement, an extraction clause, and information relating to whether an X-ray or period chart are needed, may also be included in section 30e. In addition, this bar code section may have data relating to sealants, other orthodontal information, information about exclusions, medical requirements, cosmetics, dependent age, whether a signature is on file, and a coordination rule.

Bar code section 30f contains information that is used by central claims processing unit 12 to determine whether a particular claim submitted by the subscriber qualifies for immediate adjudication, referred to as on-line adjudication. To elaborate, most health care claims can be considered as falling into one of two groups; those that are adjudicated individually, and those that are adjudicated in batches. Batch claims are normally not adjudicated immediately upon receipt by processing unit 12; but instead, these claims are held and collected by processing unit 12 until the appropriate group, or batch, of such claims is assembled, and then the whole batch of claims are adjudicated together. Claims that do not require batching may be adjudicated individually. Moreover, some of these claims can be adjudicated automatically by the insurance companies or other health care payors, immediately upon receipt of the claims without any person actually looking at or reviewing the claims. Section 30f of bar code 30 identifies those types of claims that can be made by the patient that qualify for this immediate adjudication.

Section 30g of the bar code contains transmitting and receiving data, and section 30h is provided to hold optional information. Section 30i of the bar code is provided for human readable data and, for example, this section may have the patient's name and social security number, the name of the payor, the effective dates of the plan, a code indicating the plan type, and a code indicating the printer type. Section 30j is provided for security purposes to help insure that the person presenting the card is in fact the person to whom the card was issued. For example, section 30j may contain data that can be used by telecommunications unit 24 to generate a picture of the person to whom the card was issued. Also, or alternatively, section 30j may contain data that can be used by telecommunications unit 24 to show or print a personal identification number of the person to whom the card was issued. An operator can then ask the individual presenting the card for that number to insure that the card holder is the proper card owner.

Preferably, the information in pattern 30 is encoded in a format known as PDF417, which is a two-dimensional bar code that provides a high information density and capacity. Unlike traditional linear bar codes, which typically serve as a key or address to a record in an external data base containing the required information, the portable data file is the entire data record itself—that is, all of the required information is contained in pattern 30 itself. Also, a two dimensional bar code is much like a font on the computer. Regardless of the font chosen, the information remains the same when scanned by the reader.

The PDF417 symbol format is discussed in greater detail in a brochure titled "A PDF417 Primer: A Guide To Understanding Second Generation Bar Codes And Portable Data Files," published by Symbol Technologies Inc., Holtsville, N.Y., the disclosure of which is herein incorporated by reference. The PDF417 format is also discussed in U.S. Pat. Nos. 5,319,181 and 5,337,361, the disclosures of which are also herein incorporated by reference.

Each person participating in network 10 may be given a card 32, having the appropriate data encoded thereon, when or shortly after that person purchases or is otherwise provided with an insurance policy or other coverage plan that qualifies the person for participation in the network. Then, whenever there are changes to the information on the card 32, a new card having the new or corrected information can be made and given to the card holder.

One particular advantage of issuing and using cards 32 in the above-described manner is that if errors are made in the information encoded on the cards, those errors do not necessarily impede the processing of claims made by the card holder. To elaborate, typically, central claims processing unit 12 is provided with some or all of the information on the data cards 32 of all the individuals participating in network 10. Then, when a claim for a particular person is made and data on that person's card 32 is transmitted to processing unit 12, that transmitted data is compared with the data stored on the processing unit for that person. If certain of the transmitted information, such as the claimant's social security number or the claimant's employer, does not match the corresponding data for the claimant already stored on the processing unit 12, the claim might not be processed.

In network 10, data can be processed and handled so that such a mismatch does not occur as a result of any operator error made in encoding card 32 or in entering data in processing unit 12—even if such an error actually occurs. This can be achieved in several ways. For example, when making a card 32 for an individual, an operator may input the appropriate information once into a single input device, and this one device can be used both to print that information, in the encoded format, on card 32, and to transmit that information to processing unit 12. Also, a card 32 may be encoded with the appropriate data, and then that card itself may be used as the source of the data transmitted to processing unit 12. For instance, a reader 22 may be used to transmit the data on the card to processing unit 12. In either case, the exact same data, including any errors, is both encoded on the card 32 and transmitted to claims processing unit 12. Thus, when a claim is made, the data on the card 32 matches the data in claims processing unit 12, even if there is an error in that data.

As discussed above, when a health care data transaction or insurance claim is made, reader 22 is used to read the data on portable data file 20 into telecommunications unit 24, and any suitable reader 22 may be used in the practice of this invention. Preferably, however, reader 22 is a portable device, easily held and moved by an operator.

Figure 5:
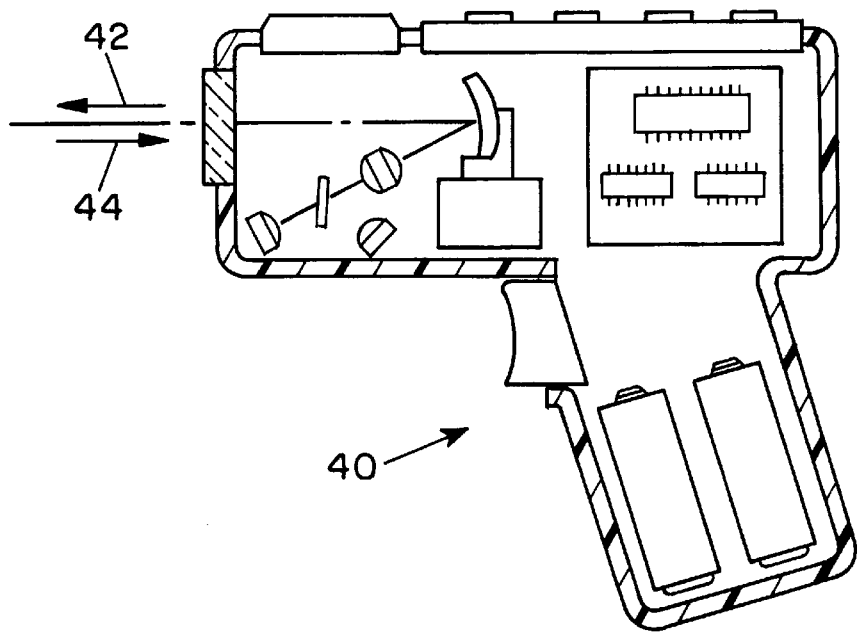
FIG. 5 illustrates a reader for reading the data file shown in FIG. 2.

As will be understood by those of ordinary skill in the art, the specific type of reader 22 that is best for use in system 10 will depend on the specific type of portable data file 20 that is used. With the preferred embodiment of system 10, in which data file 20 includes a two-dimensional bar code 30, reader 22 is a hand held, laser scanning, bar code reader, and one such reader is illustrated at 40 in FIG. 5.

With reader 40, an outgoing light beam 42 is generated in the reader, usually by a laser diode or the like, and directed to impinge upon a bar code symbol a few inches from the front of the reader unit. The reader is held by the user so that the outgoing beam 42 traverses the symbol to be read. Reflected light 44 from the symbol is detected by a light-responsive device 46 in the reader unit, producing serial electric signals to be processed for identifying the bar code. Reader 40 is described in greater detail in U.S. Pat. No. 5,399,846, the disclosure of which is herein incorporated by reference.

Figure 6:
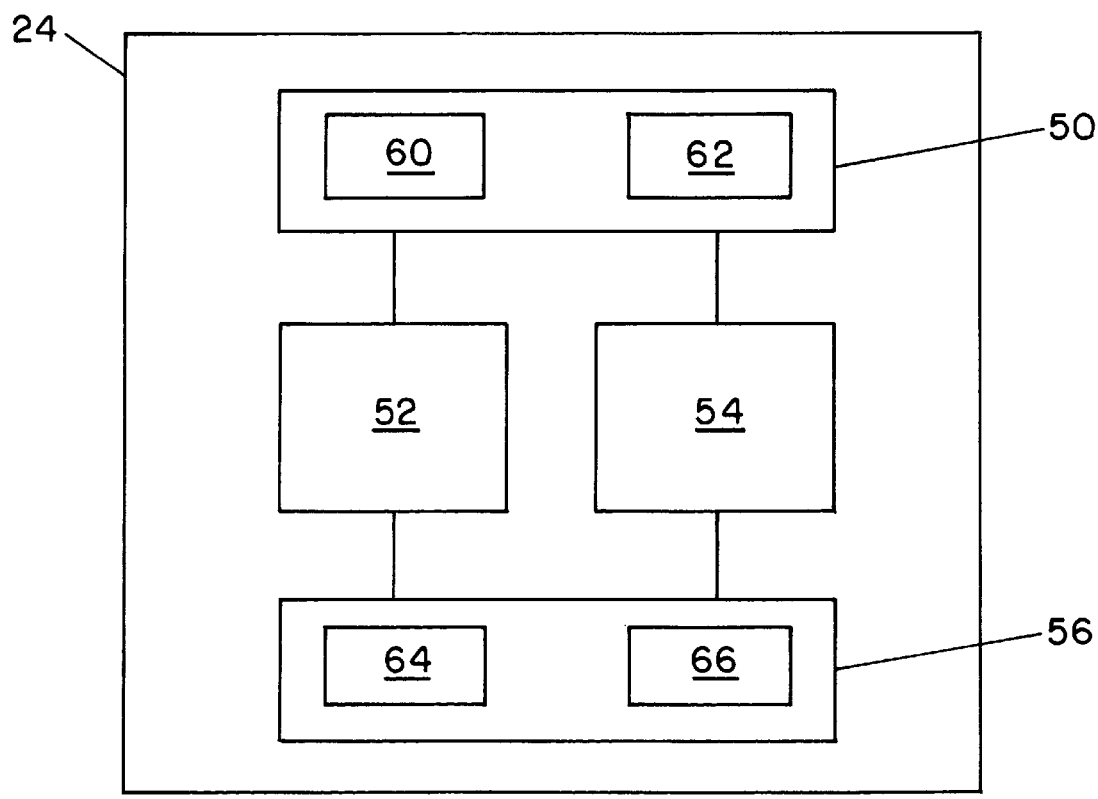
FIG. 6 is a schematic drawing of a telecommunications unit of the network shown in FIG. 1.

FIG. 6 schematically illustrates one of the telecommunications units 24 in greater detail; and as shown therein, the telecommunications unit includes input means 50, processor 52, memory unit 54 and output means 56. Input means 50 includes key pad 60 and keyboard 62, output means 56 includes screen 64 and modem 66, processor 52 includes control program 70 and prompts 72, and memory unit 54 includes claim assembly area 74. Generally, input means 50 are provided to allow an operator to transmit data to the processor 52 and memory unit 54, and output means 56 is provided to enable the processor to transmit and display data. Prompts 72 are used to solicit input data from an operator, and assembly area 74 is provided for assembling the electronic claim form. Control program 70 is provided to control the operation of telecommunications unit 24; and more specifically, the control program controls the presentation of prompts 72 and the collection and assembly of data into the electronic transaction or claim form. Also, after the electronic data transaction or claim form is assembled, the control program, for example in response to a command signal from an operator, transmits that electronic data set to central claims clearinghouse 12 via suitable transmission means.

Figure 7:
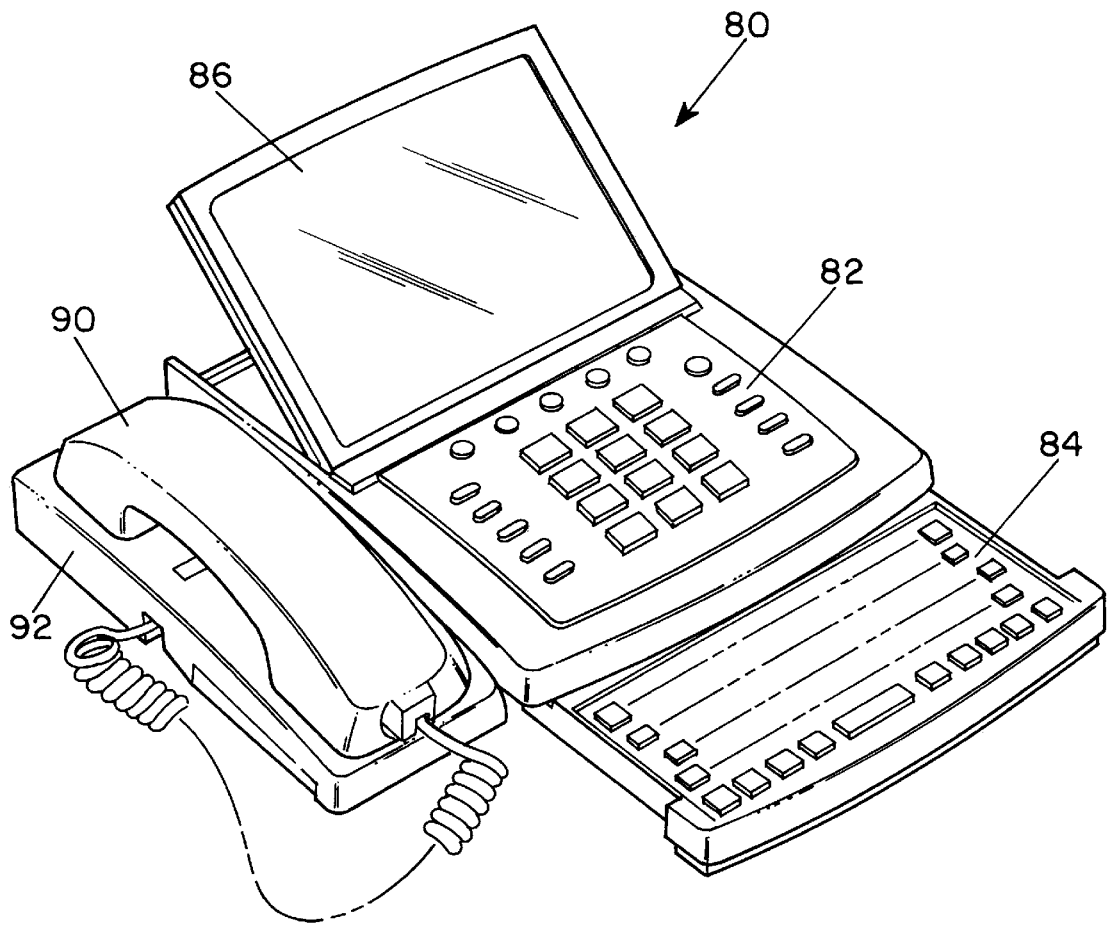
FIG. 7 shows a preferred telecommunications unit for the network of FIG. 1.

Any suitable telecommunications unit 24 may be used in the practice of the present invention. One telecommunications unit that is very well suited for system 10 is available from Philips Home Services, Inc., under the product name "Philips Screen Phone," and FIG. 7 shows this unit 80. The "Philips Screen Phone" is a screen telephone with the flexibility of a computer, and an important advantage of this unit is that a computer novice can comfortably accomplish electronic communications with it on the first try.

As shown in FIG. 7, this telecommunications unit 80 includes a plurality of input means, including key pad 82 and keyboard 84, and a plurality of output means, including video screen 86, telephone 90 and modem 92. This unit also includes a processor and a memory unit that are not shown in FIG. 7. Key pad 82 is used to operate telephone 90, and both the key pad and keyboard 84 are used to input data to the processor and the memory section of the telecommunications unit and to operate video screen 86.

As mentioned above, the data obtained from the personal portable data file 20, via reader 22, completes a first part of the electronic transaction or claim form. In order to complete the rest of the electronic transaction or claim form, an operator supplies information about the service or treatment received by the patient, and prompts 72 are provided to solicit the desired information.

More particularly, prompts 72 are computer routines or subroutines, stored in processor memory 54, that are used, under the control of control program 70, to form output representations that prompt an operator to provide the desired data to processor 52. These output presentations may take any suitable audio or video format that is human understandable. For instance, processor 52 may present the prompts as images on screen 86, with the operator interacting with the screen to respond to the prompts. This interaction, may be, for example, via a keyboard, via a controlled cursor on the screen, or via the combination of a keyboard and a controlled cursor.

The prompts 72 may have a variety of specific forms. For instance, a prompt may give the operator a series of choices, and the operator responds to such a prompt by selecting one of those choices. As another example, a prompt may present a question or a command for certain information, and the operator responds to such a prompt by answering the question or providing the commanded information. Also, these prompts may include words or phrases presented in a truncated or abbreviated manner, with the operator being trained or experienced to understand the meaning of the truncated presentations.

Preferably, these prompts are presented in such a way that they can be completely responded to with a minimum of words, allowing an operator to respond fully to each prompt with just one, or at most a few, input signals. Also, these prompts are presented to the operator one at a time, according to a predetermined program. Moreover, such a predetermined program may be designed so that the response to one prompt may determine which prompt is presented next, or whether a particular prompt or prompts are skipped.

Information, including responses to prompts 72, may also be input to telecommunications unit 24 by using reader 22 to scan bar codes that contain the information in a machine readable format. In particular, as discussed below, for various prompts, the complete response to the prompt is one of a known number or sets of data. For example, a prompt may request the name, address and other information about a treating physician at the health care facility. Since there are a limited number of physicians at each facility, there are, thus, a limited number of responses to the prompts.

The operator may be provided with bar codes having these responses encoded therein in a machine readable format; and, in particular, each of these bar codes may contain all the data for a respective one response. These bar codes may be either one-dimensional or two-dimensional bar codes. To respond to the prompt, the operator simply identifies the bar code having the appropriate responsive data, and scans reader 22 across that bar code to input the data in the bar code telecommunications unit 26. This procedure for inputting information is particularly advantageous because it reduces, and may even eliminate, the need to use a keyboard to input information. This, in turn, substantially simplifies the operation of the telecommunications unit.

For example, FIG. 8 is a chart having a variety of bar codes that may be used to input information to the telecommunications unit in response to various prompts. A first group of these bar codes contain information relating to various specific teeth, a second group of the bar codes have information about specific procedure that may be performed on the teeth, and a third group of the bar codes have other information that may be scanned to help complete the electronic claim form.

With the preferred embodiment of control program 70 described herein in detail, the treatment information needed to complete an electronic transaction or claim form is comprised of two types of information, referred to as general treatment information and specific treatment information.

General treatment information refers to information that a patient is typically asked when preparing an insurance claim form and that relates to the injury or illness for which treatment is sought but which may vary from patient to patient, even for the same type of injury or illness. For example, such general information may include whether an injury is an occupational injury, whether X-rays will be required, whether the patient has secondary insurance, whether the patient has signed a release, and whether Medicare covers the treatment.

Specific treatment information is information that is related to or describes a particular treatment that the patient receives. For example, this information may include a specific identification of the illness or injury for which the patient is treated, a general category in which the treatment may be classified, a more specific description of that treatment and a fee or charge for that treatment. If the treatment is comprised of a number of specific procedures, the specific treatment information may include a description of the above-mentioned features for each of these specific procedures.

Figure 9A:
FIGS. 9A–9D show several screens that may be shown as a claim is assembled in the telecommunications unit.
Figure 9B:

FIGS. 9A and 9B show, as an example, two screens that may be presented to an operator to obtain general treatment information. With reference to FIG. 9A, the term "X-rays" represents the question: "Will the doctor's office be submitting X-rays with the claim"? and the term "Occupational Injury" represents the question: "Is this patient being treated for an occupational injury"? The items on the screen are numbered. These questions may be answered automatically on the screen with the most probable answer; and if the actual answer is different, the operator simply pushes the keypad number and the answer changes, for example, from "yes" to "no" or from "no" to "yes." The telecommunications unit may also be designed and operated so that the operator responds to each item by, first, entering the item number and then entering "yes" or "no."

If in response to the prompt of FIG. 9A, the operator indicates that the patient has secondary insurance, processor 22 then shows the screen of FIG. 8B on the screen. This screen contains a column of words or phrases, each of which represents a standard question or command. For instance, the word "name" represents the command: "Enter the name of the secondary insurer," and the phrase "Group #" represents the command: "Enter the group number of the policy of the secondary insurer."

To respond to the prompt of FIG. 9B, the operator enters, for example via a keyboard, the proper response to each command. For instance, the response to each command may be entered on the same line on the screen as the command itself, producing the screen shown in FIG. 9C.

Figure 9C:
Figure 9D:

After the operator completes the response to the screen of FIG. 9B, which produces the screen of FIG. 9C, the control program 32 may present the screen shown in FIG. 9D. This screen, like screens 9A and 9B, contains a column of words and phrases, each of which represents a specific question or command. With the screen of FIG. 9D, each represented command or question is identified by a respective one number, and the operator responds to each of these items by entering the identifying number for the item and then entering the response to the item. For instance, the word "Provider" in FIG. 9D represents the command: "Enter the name of the individual who provided the treatment or services to the patient," and the operator responds to this item by entering the number "7" and the entering the name of that individual.

Figure 10A:
Figure 10B:

FIGS. 10A–10H show various screens that may be presented to an operator to obtain specific treatment information about, as an example, a dental procedure. FIG. 10A shows, simply, the words "Tooth Number," and in response to this prompt, the operator inputs a standard number identifying a tooth being treated. After a response is received to the screen of FIG. 10A, program 70 shows the screen of FIG. 10B on the video monitor. This screen contains the words "Tooth Surface," and in response to this prompt, the operator inputs a standard abbreviation identifying a surface area of the tooth that is being treated.

Figure 10C:
Figure 10D:
Figures 10E, 10F:
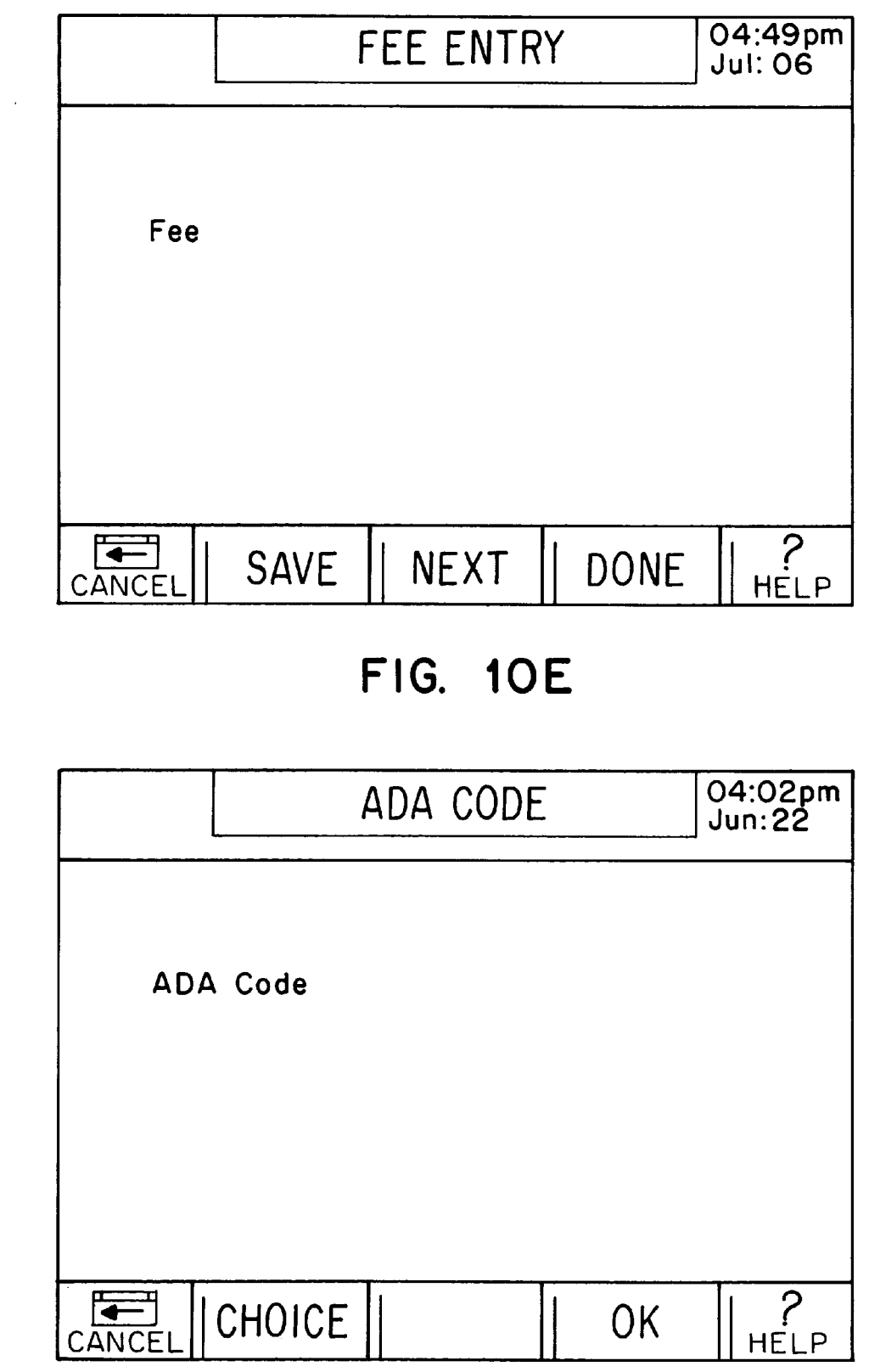
Figure 10G:
Figure 10H:
Figure 11A:
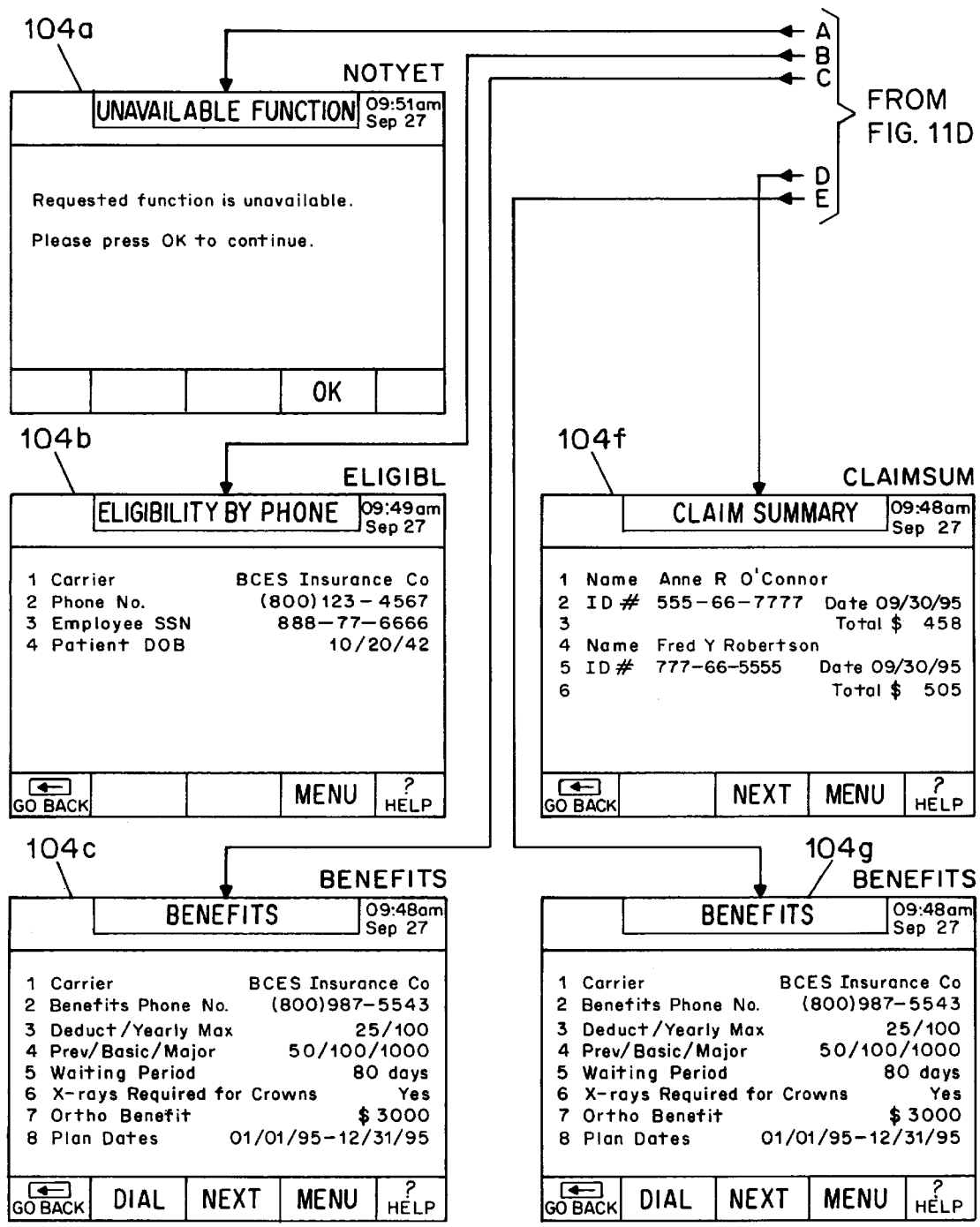
FIG. 11 shows various screens that may be displayed on the telecommunications unit.
Figure 11B:
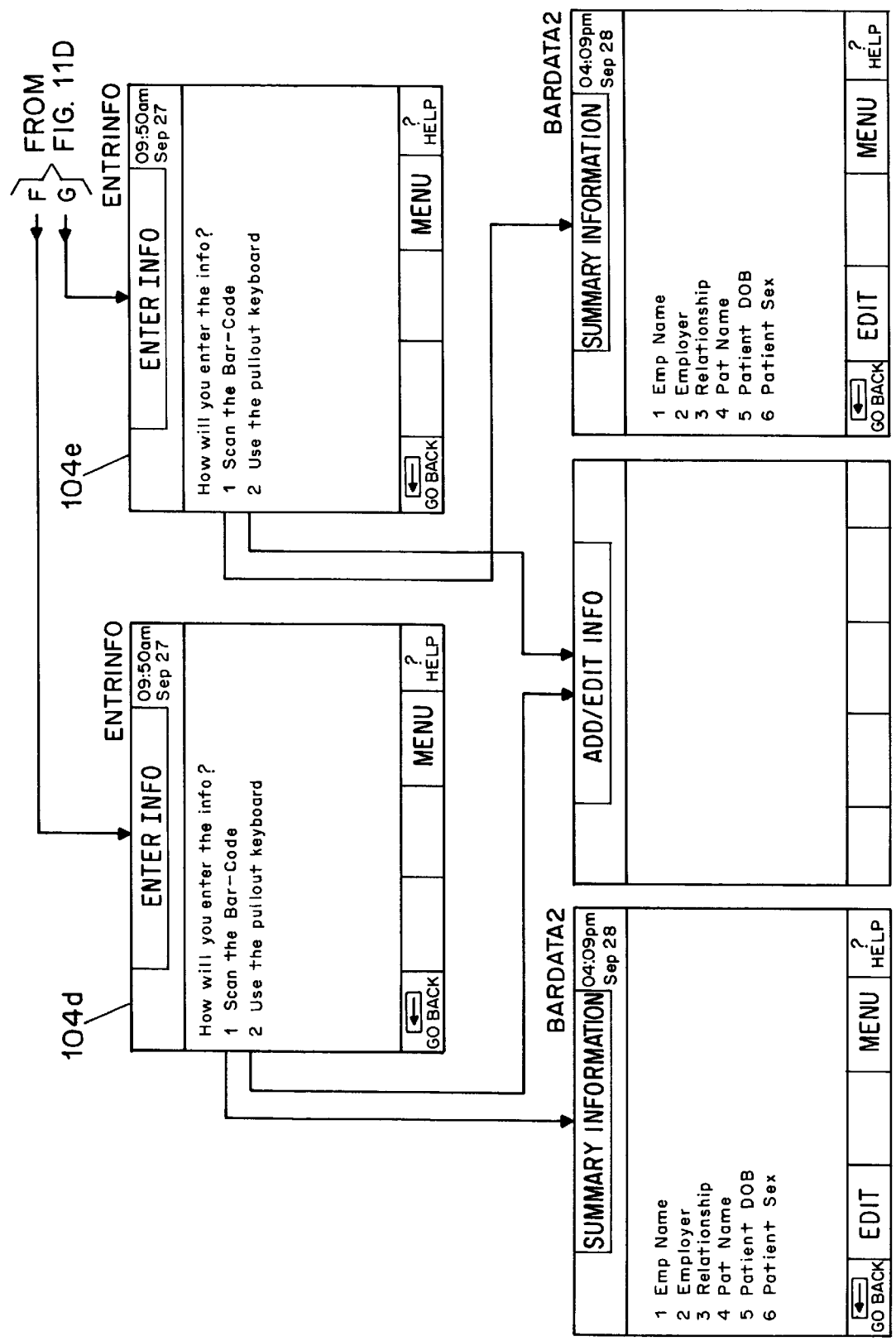
Figure 11C:
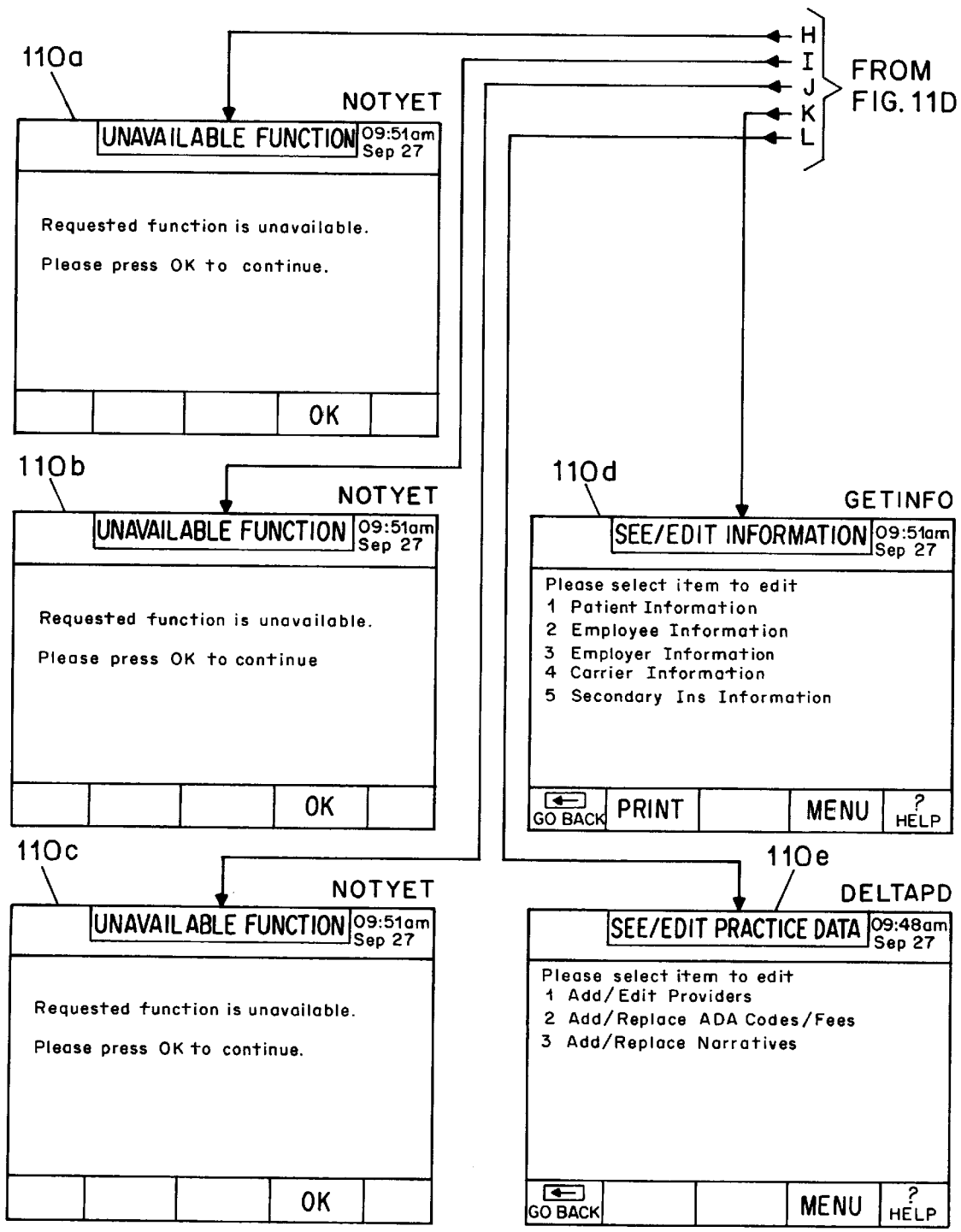
Figure 11D:
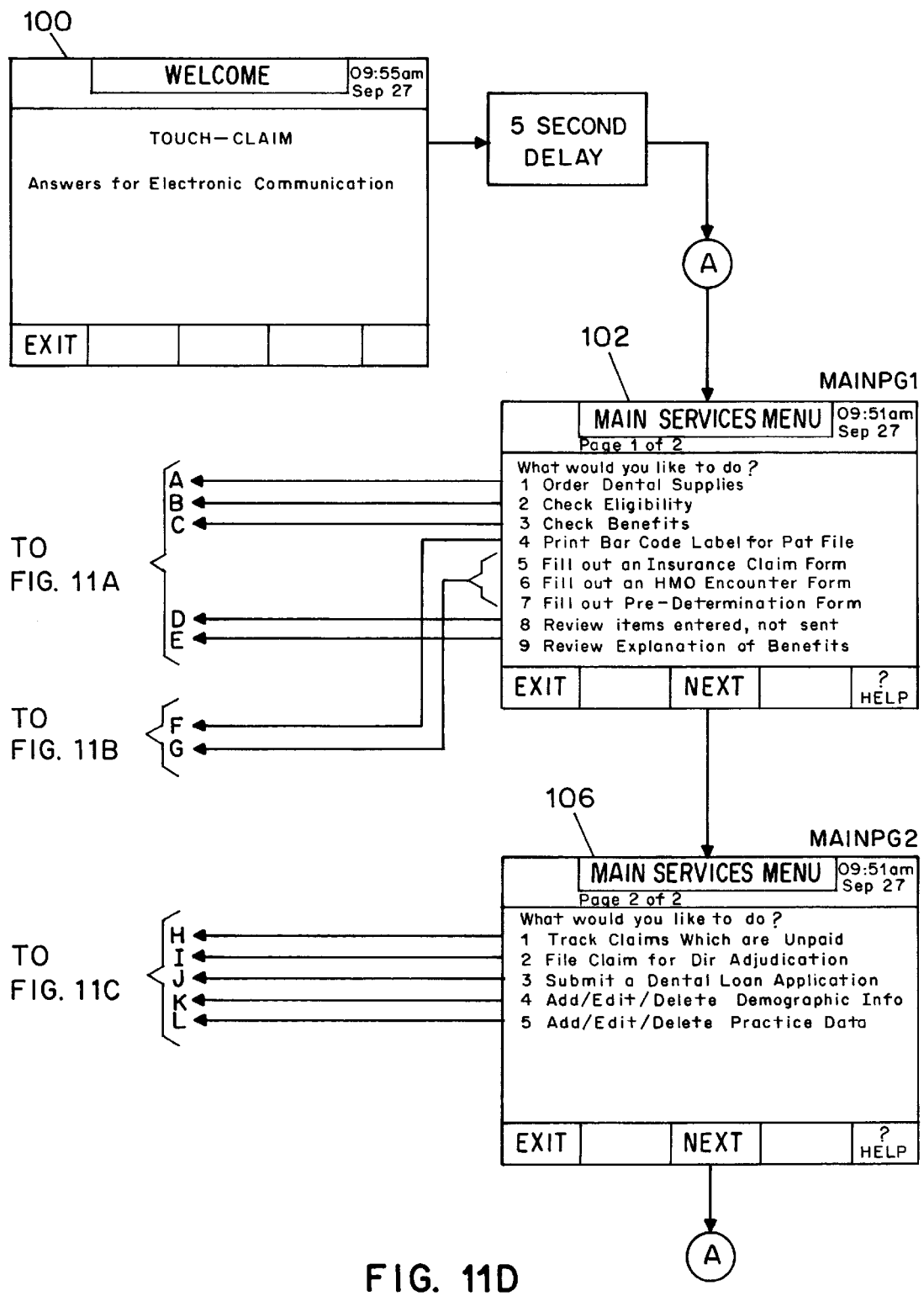
Figure 12A:
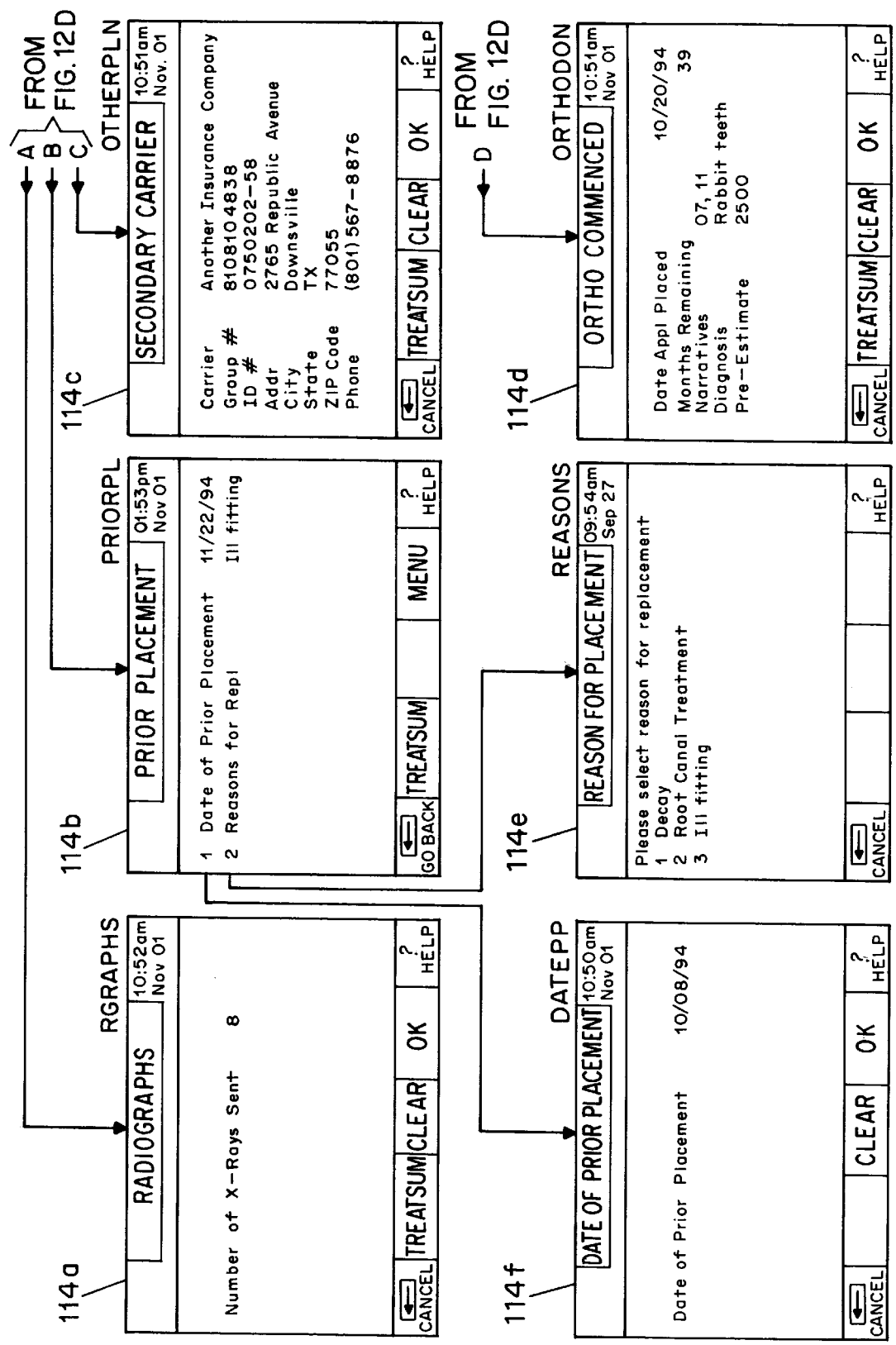
FIG. 12 illustrates screens that may be displayed on the telecommunications unit to prompt an operator to provide information needed to assemble an insurance claim.
Figure 12B:
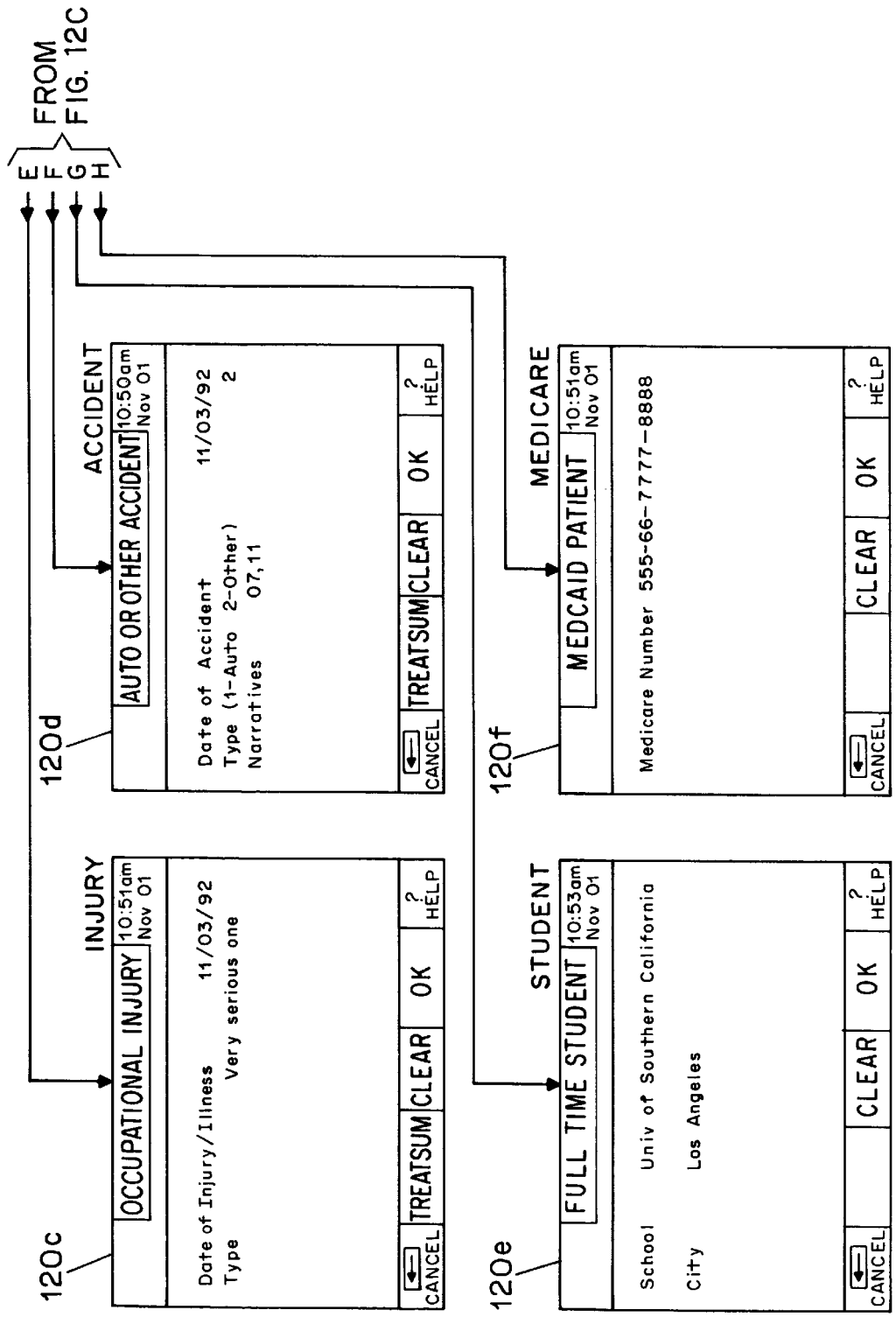
Figure 12C:
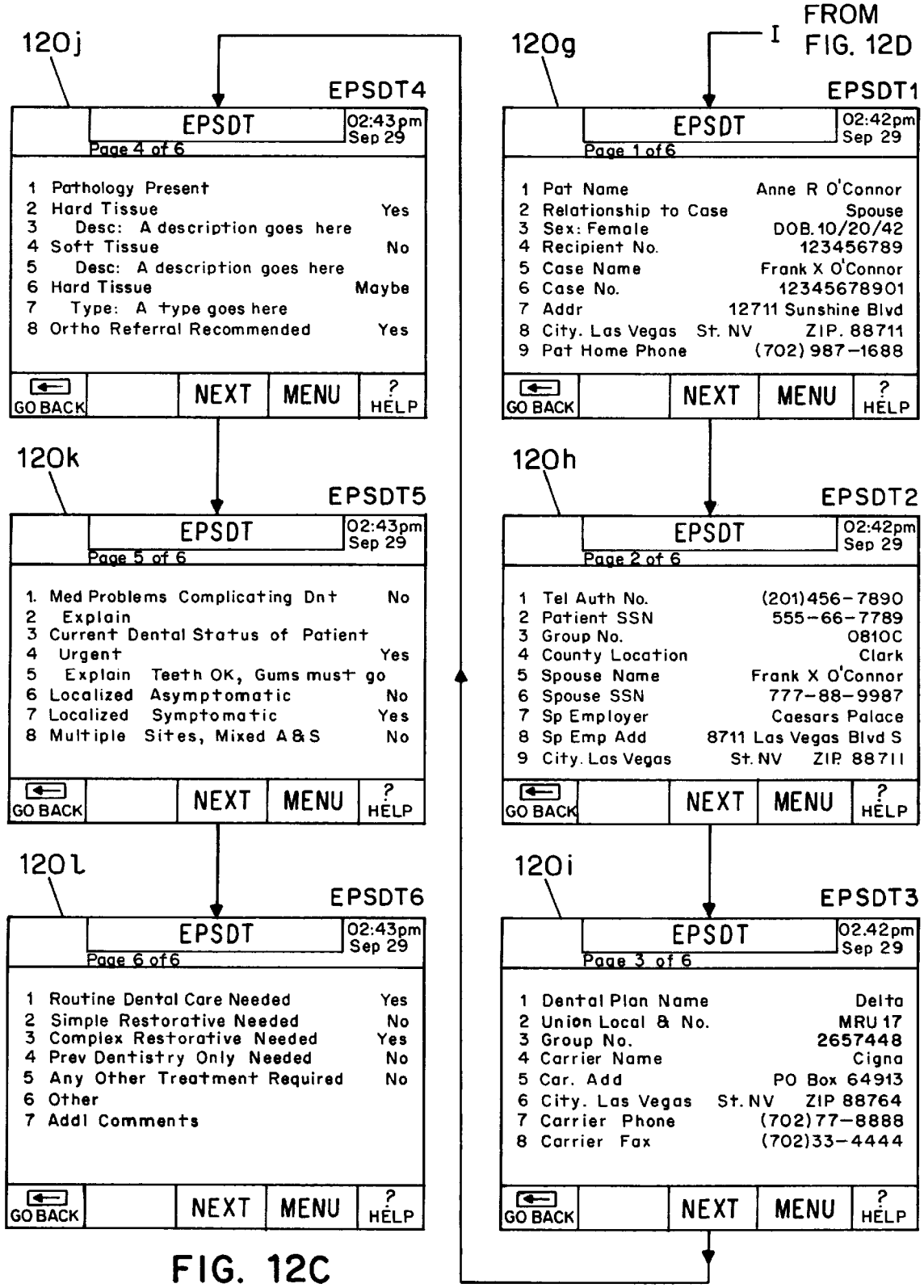
Figure 12D:
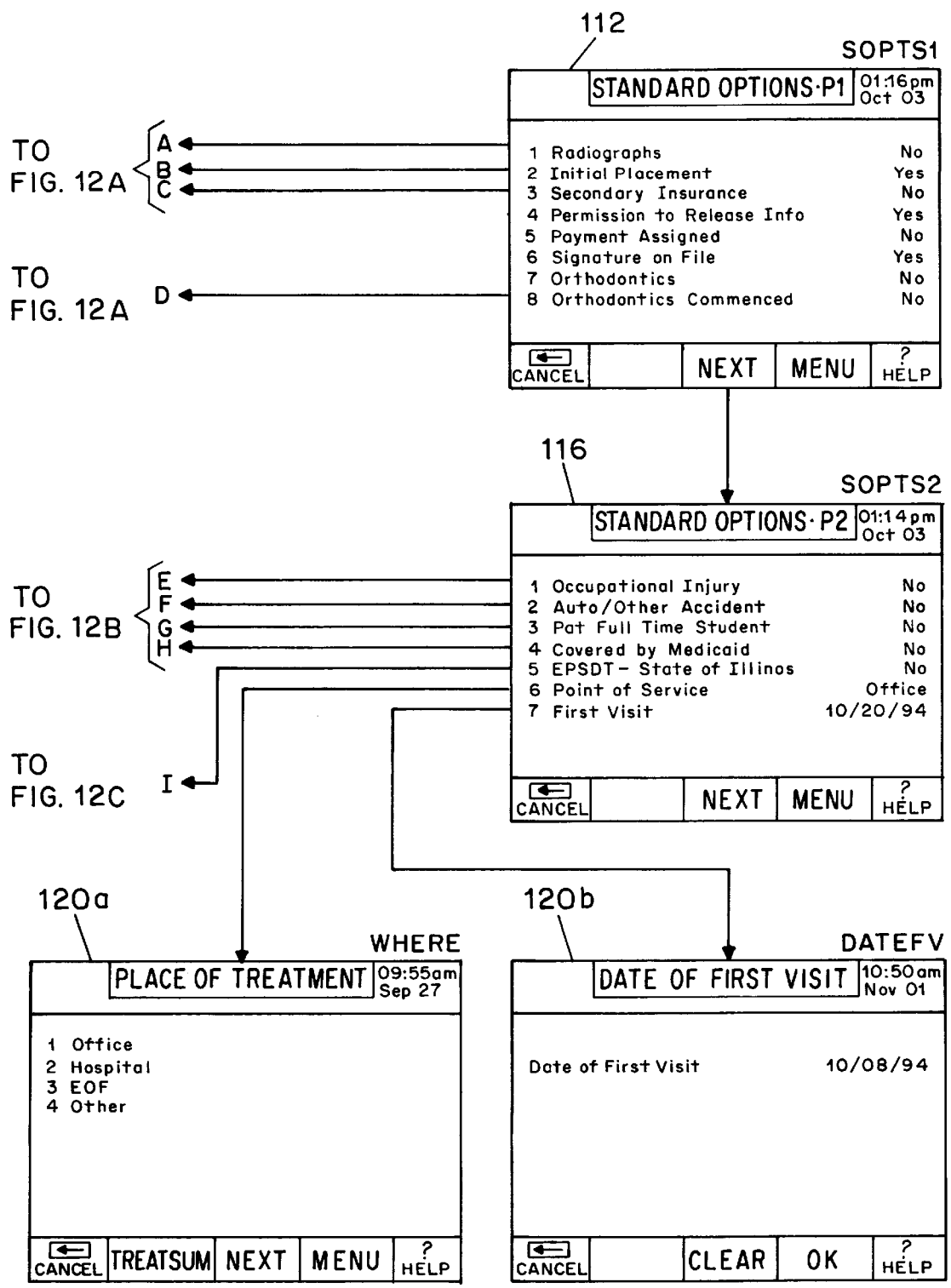
Figure 13A:
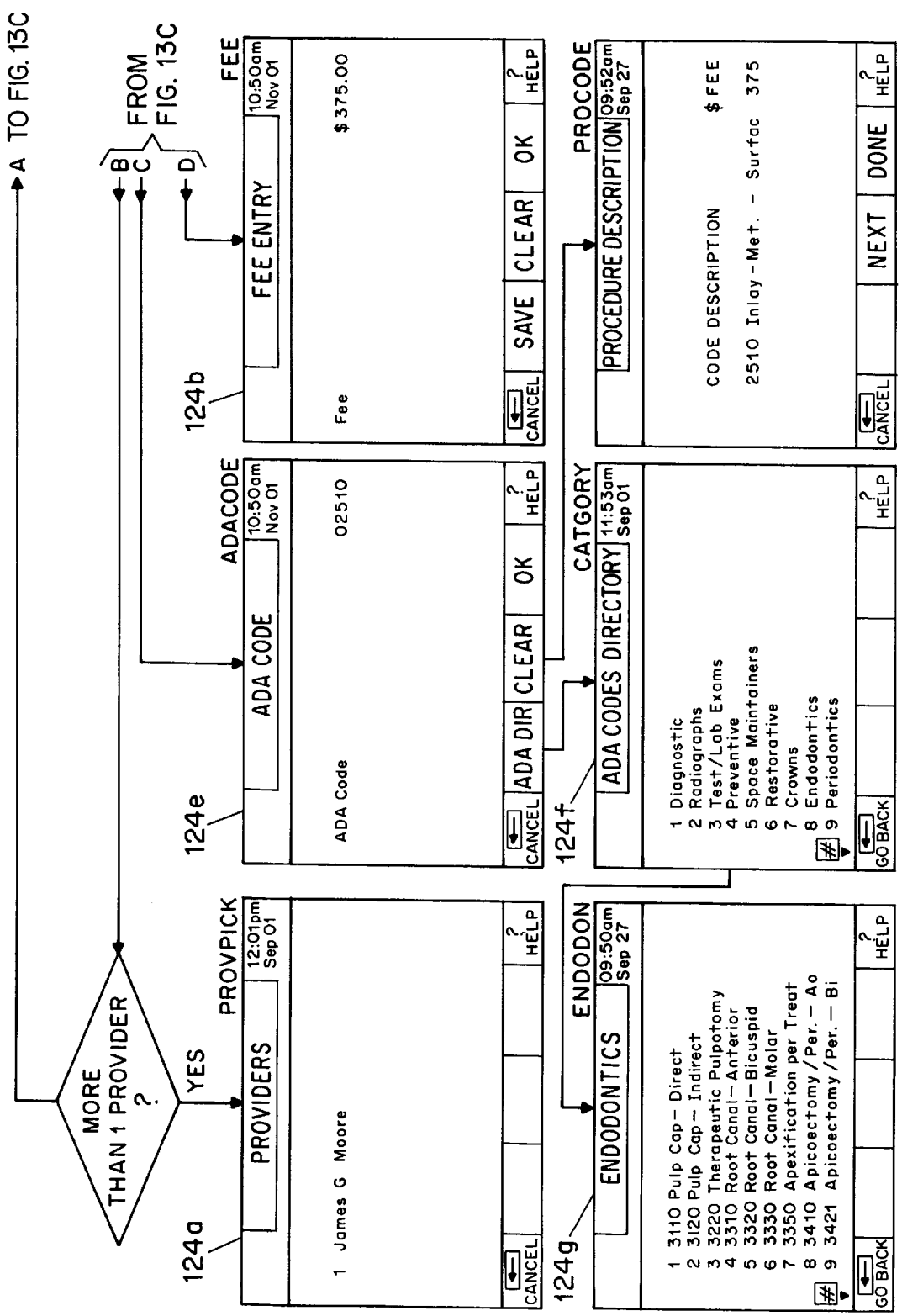
FIG. 13 shows additional screens that may be displayed to obtain additional information from an operator.
Figure 13B:
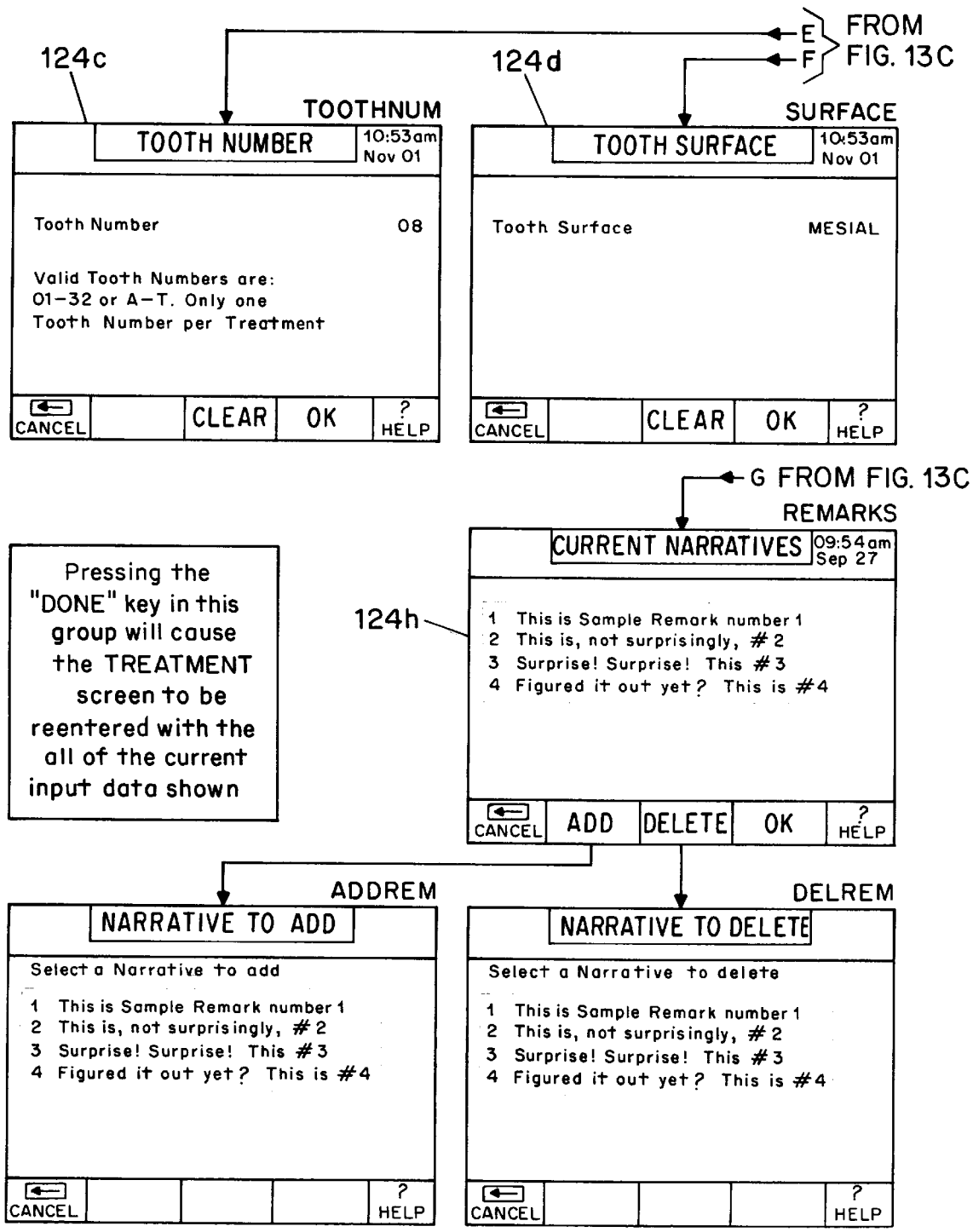
Figure 13C:
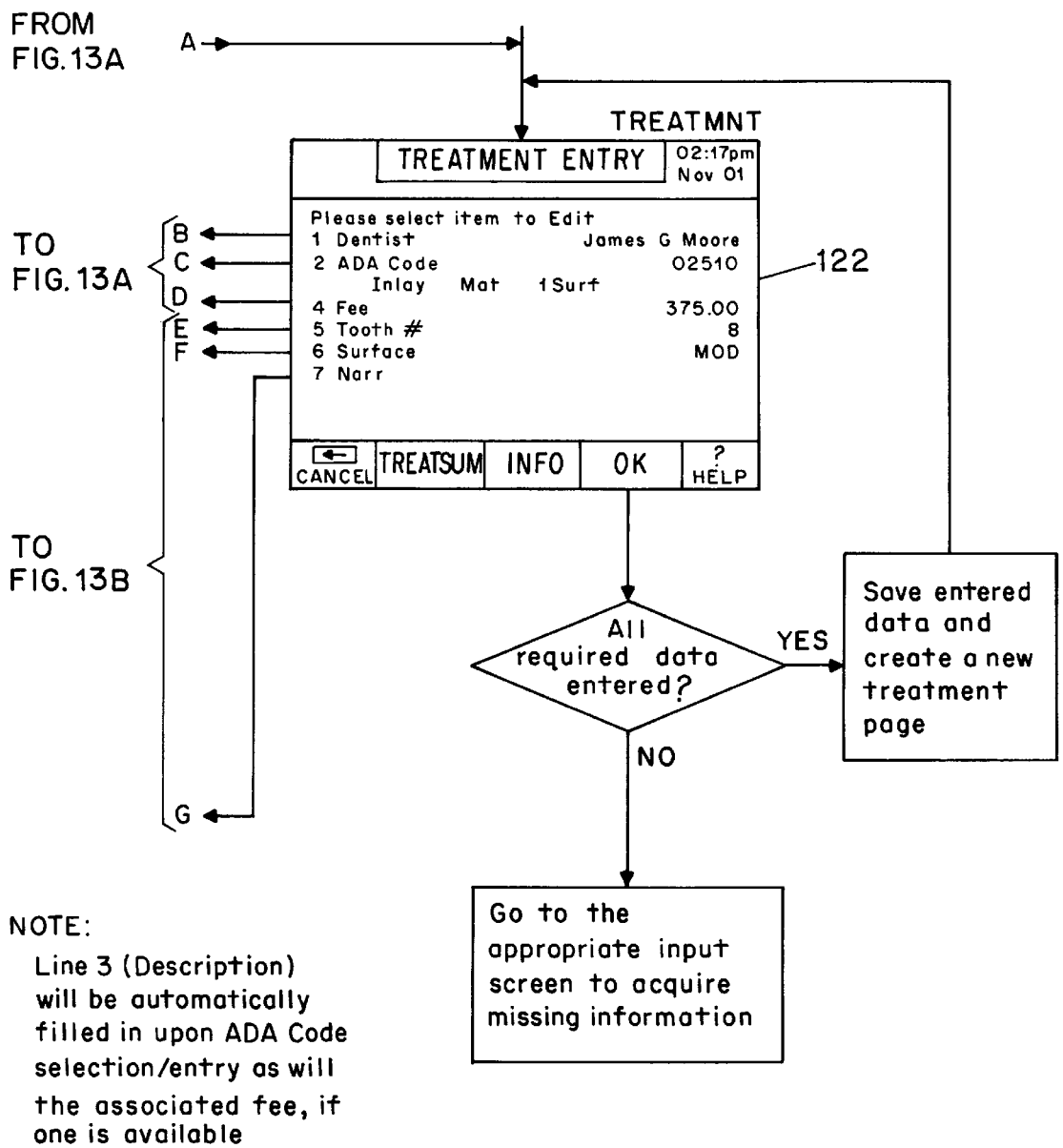

FIGS. 10C and 10D show screens that present the operator with a series of choices, and the operator responds to each of these screens by selecting the appropriate choices. Any specific procedure may be used to do this. For example, the screen of FIG. 10C lists various general categories of procedures, each one being identified by a different number, and the operator may indicate the general category of the procedure that the patient receives by entering the number of that category.

A series of more specific procedure categories may be associated with each general category shown in the screen of FIG. 10C. Each of these series of more specific procedure categories may be shown on a respective one screen, and preferably program 70 is designed to show automatically the screen having the more specific categories of the one general category selected by the operator on the screen of FIG. 10C.

For example, the screen of FIG. 10D shows a set of more specific categories of the general category "Restorative" shown in FIG. 10C. Whenever an operator selects "Restorative" on the screen of FIG. 10C, the screen of FIG. 10D is shown. Each of the categories shown in FIG. 10D is also identified by a specific number, and the operator indicates the specific category of the procedure that the patient receives by inputting the number for that specific category.

After the operator responds to the screen of FIG. 10D, program 70 presents screens 10E–10H, one at a time and in sequence. In response to the screen of FIG. 10E, the operator inputs a fee amount if none is shown; and in response to the screen of FIG. 1OF, the operator inputs an American Dental Association code for the procedure. After this is done, the control program presents the screen of FIG. 10G, which contains a short list of words that represent questions or commands. For example, the word "Code" represents the command: "Enter the standard code number for the procedure." The operator enters the appropriate response to each command on the same line as the command. After the operator completes the response to the screen of FIG. 10G, program 70 presents the screen of FIG. 10H. This screen presents a summary of the specific treatment information that has been inputted, and is provided to give the operator an opportunity to correct or delete any incorrect information. Any acceptable procedure or subroutine may be used to correct or delete the information. If the information on the screen is correct, the operator inputs a confirm signal to processor 52.

As the treatment data is being input to processor 52, control program 70 assembles that data, along with the patient related data, in the electronic transaction or claim form. When that form is completed, the operator inputs a transmit command to processor 52, and in response, this processor transmits that electronic transaction or claim form to central claims clearinghouse 12.

As will be understood by those of ordinary skill in the art, any suitable transmission means may be used to transmit the electronic claim form to processing unit 12. In a typical application, the processors 52 and 12 are located a substantial distance from each other; and preferably, system 10 incorporates a common carrier, such as a commercial telephone line, to transmit the data between these two processors. A standard modem may be used to convert the data signals from processor 52 into the appropriate signals for transmission over the telephone lines.

Upon receipt of the electronic transaction or claim form, clearinghouse 12 checks to be sure that all necessary data has been submitted pursuant to the patient's insurance policy or other coverage plan. If complete, the claim may then be transmitted to the insurance company or other health care payor, who may determine if payment for the services received by the patient is appropriate, and if so, the appropriate amount of the payment, the payor and the payee.

System 10 may be designed so that if payment is appropriate, processor 26 initiates a procedure to make that payment. For example, processor 26 may transmit a command to a printer to print a check for the appropriate payment.

FIGS. 11–21 illustrate a specific example of a claims assembling program that may be operated on the individual telecommunication units 24. With reference to FIG. 11, upon start-up of the unit, Welcome Screen 100 is shown; and after a short delay, screen 102, referred to as the Main Services Menu screen, is shown on the screen. This latter screen lists the tasks or routines that can be performed in addition to the claims assembling program. All these tasks use the base data that comes form the data file. Each one of these tasks can be accomplished by different computer data manipulations by the telecommunications unit 24.

Screen 102 lists eight tasks or routines: (1) ordering dental supplies, (2) checking the eligibility of the claimant, (3) printing the bar code on the claimant's data card 32, (4) filling out an insurance claim form, (5) filling out an HMO encounter form, (6) filling out a predetermination form, (7) reviewing items entered by the operator prior to transmitting those items to central claims clearinghouse 12, and (8) providing a review of an explanation of various available benefits. A number is provided on screen 84 to identify each of these routines; and to start a specific routine, the operator inputs the number identifying that routine. For example, to start the routine to order dental supplies, the operator would input "1"; and to start the routine to check the eligibility of the claimant, the operator inputs "2."

When the operator inputs a particular number, the claims assembling program displays one of the screens 104*a* through 104*g*. In particular, if the operator inputs 1, 2, 3, 4, 8 or 9, screens 104*a*, 104*b*, 104*c*, 104*d*, 104*f* or 104*g*, are, respectively, shown on the monitor 86; and if the operator inputs either 5, 6 or 7, screen 104*e* is shown on the screen. Screens 104*b*, 104*c*, 104*e* and 104*g* prompt the operator for additional data. Screen 104*f* shows a summary of information that has been input to the telecommunications unit and provides the operator with the opportunity to change or correct any of this data.

In case a single screen is not large enough to show all of the desired routines, the Main Service Menu may be provided with a second page 106, and this screen may be displayed by entering an appropriate command while screen 104 is shown. Screen 106 lists five additional tasks: (1) tracking unpaid claims, (2) filing claims for direct adjudication, (3) submitting a loan application, (4) adding, editing or deleting demographic data, and (5) adding, editing or deleting practice data. Here too, a number is provided on screen 106 to identify each of these tasks; and to start one of these tasks, the operator inputs the number of that task. If the operator inputs 1, 2, 3, 4 or 5, screens 110*a*–110*e* are shown respectively.

To enter the general treatment information, the operator transmits a signal to processor 52 to initiate this routine. Upon receipt of this signal, the claims assembling program shows the screen 112 in FIG. 12 on video monitor 64. This screen, referred to as the Standard-Options-P1 screen, lists various questions that the operator answers. These questions may be presented in a truncated or abbreviated form, so that, for example, the term "radiographs" means: Is the doctor submitting X-rays? Each question on the screen is identified by a number, and the operator responds to the screen by entering each question number, and after each number is entered, entering "yes" or "no."

For some of the questions on screen 112, depending on the response, additional information may be needed; and if this is the case, the claims assembling program will automatically show one or more screens to obtain this additional information. In particular, if the response to questions 1, 2, 3 or 8 of screen 112 is "yes," then screens 114*a*, 114*b*, 114*c* and 114*d* are shown respectively. Screen 114*a* requests information about X-rays, screen 114*b* requests data about prior placement, screen 114*c* prompts the operator for data about secondary insurance, and screen 114*d* solicits information about orthodontal treatment.

Screens 114*a*–114*d* may not be sufficient to obtain all of the desired information, and if this is the case, additional screens may be displayed to obtain the needed data. For instance, in case there had been a prior placement of the patient, screens 114*e* and 114*f* may be shown after screen 114*b* is shown to obtain the reason for and the date of that prior placement.

After all the questions on screen 112 have been completely answered, the operator enters a signal to confirm that this has been done; and then the claims assembling program shows screen 116, referred to as the Standard-Options-P2 screen. This screen, like the Standard-Options-P1 screen, lists a series of questions in an abbreviated or truncated manner. For instance, the phrase "auto/other accident" means: is the patient being treated for an injury caused by an automobile or some other type of accident?" and the phrase "first visit" means: "what was the date of this patient's first visit to this office."

Some of the questions on screen 116 are multiple choice questions—that is, they require that the operator provide one of several preset choices for the answer. For each of these questions, the claims assembling program may include a screen that lists the possible predetermined choices from which the operator can choose to answer the question. For instance, screen 120*a* shows the choices that the operator has to answer question number 6 on screen 116. As shown on screen 120*a*, the operator can choose from (1) office, (2) a hospital, (3) an emergency operating facility, and (4) some other place.

Some of the questions on screen 116 might require data that had been previously entered; and for each of these questions, the claims assembling program may include a screen that displays this data. For example, screen 120*b* shows the answer to question 7 on screen 116—the date of the patient's first visit to this office. If the patient had not previously visited this office, then to respond to question number 7 on screen 116, the operator enters a command to show screen 120*b*, and the operator then enters the date of the patient's first visit. This data may then be stored in the patient's personal data file so that it is available the next time the patient visits the office.

Also, for some of the questions on screen 116, additional information may be needed depending upon the response to the question; and if such additional information is required, the claims assembling program will automatically show one or more screens to prompt the operator to provide the needed data. In particular, if the responses to questions 1–5 on screen 116 indicates that more data is required, screens 120*c*–120*g*, respectively, are shown on video monitor 86. Screen 120*c* requests more information about an occupational injury, screen 120*d* solicits data about an automobile or other accident, and screen 120*e* prompts the operator to provide data about a patient who is a full time student. Screen 120*f* requests certain information about Medicaid patients, and screen 120*g* asks for certain information needed to process claims for Illinois residents. Some of the screens that request this additional information may have more than one page; and as an example, FIG. 9 shows six pages of screens 120h–120l to obtain the information needed to process claims for Illinois. residents.

After the operator has fully responded to the questions on screen 116 of FIG. 11, the operator enters a signal to indicate that this has been done. In response, the claims assembling program then shows screen 122 of FIG. 13. This screen, referred to as the Treatment Entry Screen, lists various questions or prompts that are used to obtain the specific treatment information. In this example, the Treatment Entry screen requests information about a dental procedure, and specifically, a tooth amalgam. More specifically, the screen requests the dentist's name, the ADA code for the procedure, the fee for the procedure, a tooth identification number, a description of the treated tooth surface, and a brief narrative describing the treatment. Each item on screen 122 is identified by a number; and to enter the specific treatment information, the operator enters the numbers 1–7, and, after each number, the operator enters the appropriate response. This entry may be accomplished by simply scanning an appropriate bar code, in the manner discussed above, or by using the keyboard.

Preferably, each response is selected from a group of predetermined possible responses, and screens having these possible responses may be shown to help the operator provide the appropriate responses. For instance, screen 124a shows a list of the providers, and screen 124b shows a list of fees. Screen 124c shows the range of tooth numbers, and screen 124d shows descriptions of teeth surfaces.

To respond to item number 2 on screen 122, the operator enters the ADA code for the procedure received by the patient. If the operator does not know the appropriate ADA code for this procedure, the operator enters a signal that instructs the claims assembling program to show screen 124e, and then the operator enters a signal to show screen 124f. This latter screen lists various general categories of procedures. Each of these general categories is identified by a number, and the operator then enters the number of the general category of the procedure performed on the patient. For purposes of this example, the operator selects category 8, which is "Endodontics." In response to this entry, the claims assembling program shows screen 124g, which contains a list of specific types of endodontic treatments and the ADA code for each of these specific treatments. Each of these specific treatments is also identified by a number on the screen 124g, and the operator enters the number for the treatment. After this entry has been made, the claims assembling program shows the Treatment Entry Screen, with the identified data for tooth number, surface and ADA code appearing on the screen.

Screens 124h–124j are provided to help the operator complete the narrative portion of screen 122. More specifically, screen 124h shows several basic narrative statements, screen 124i shows several statements that can be added to the narrative, and screen 124j shows several statements that can be deleted from the narrative. To use screen 124h, the operator enters a signal that instructs the program to show this screen. Each of the basic narrative statements on the screen is identified by a number, and the operator enters the number of the basic narrative statement that he or she wants to use.

The operator can add one or more of the statements shown on screen 124h to the basic narrative. To do this, the operator enters a signal that instructs the processing program to show screen 124i and the operator inputs the number or numbers associated with the statements shown on this screen that the operator wants to add to the basic narrative. The operator also has the ability to delete one or more of the statements shown in screen 124i from the basic narrative. To do this, the operator enters a signal that instructs the claims assembling program to show screens 124i, and the operator inputs the number or numbers associated with the statements on that screen that the operator wants to delete from the formed narrative.

After the specific treatment information has been entered for a particular treatment received by the patient, the operator inputs a signal to indicate that this has been done. The claims assembling program then shows a new Treatment Entry Screen. A respective one Treatment Entry Screen is completed for each specific treatment or service received by the patient that will be included in the same insurance claim or transaction.

After all of the specific treatment information for all of the services received by the patient have been entered, the operator inputs a signal to indicate that this has been done. The claim information is then saved to an electronic storage area in the telecommunication device for later transmission to the clearing house. In response, the claims assembling program returns to the Main Menu Screen 102.

Figure 14A:
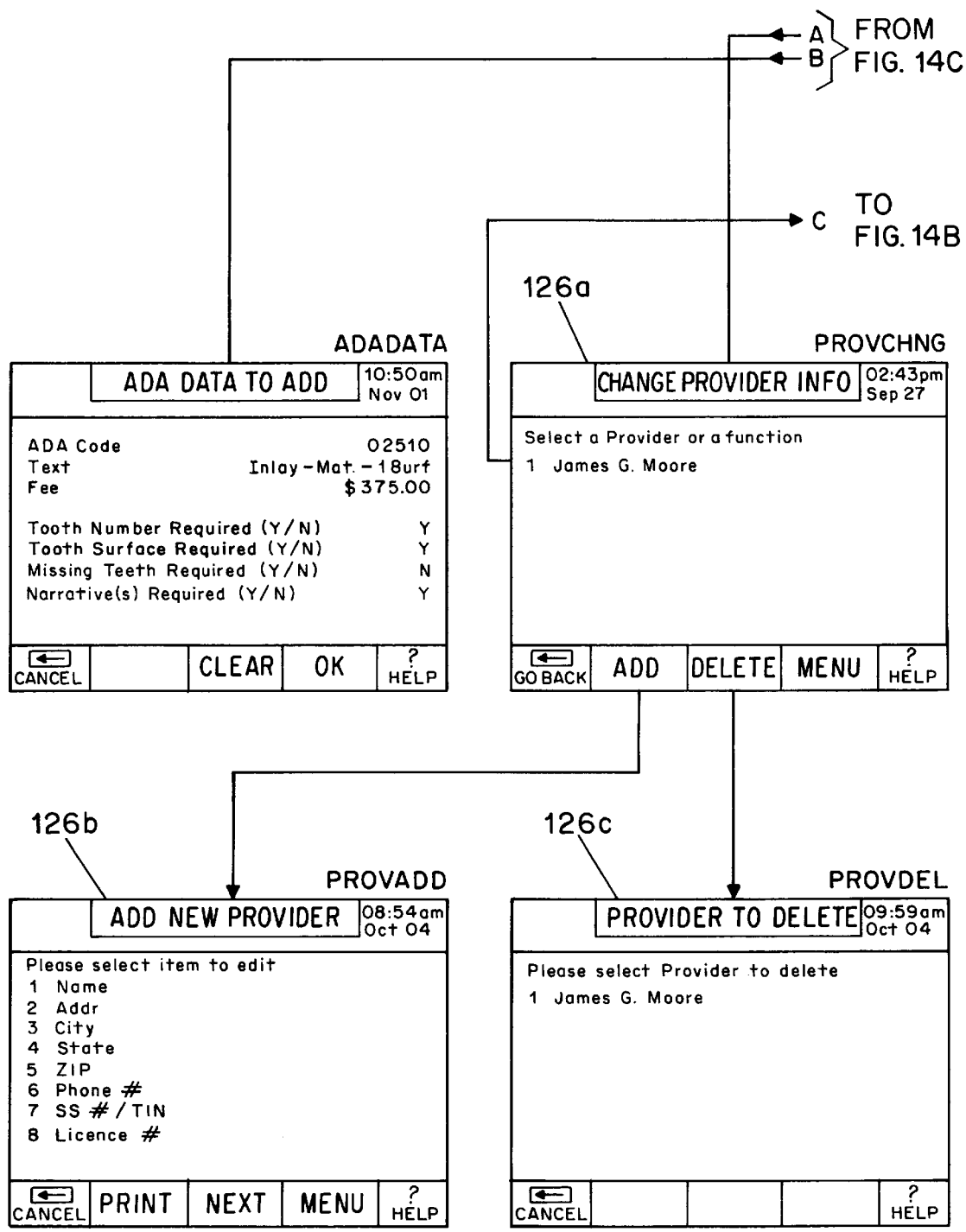
FIG. 14 shows screens that may be shown to help an operator change data on file in the telecommunications unit.
Figure 14B:
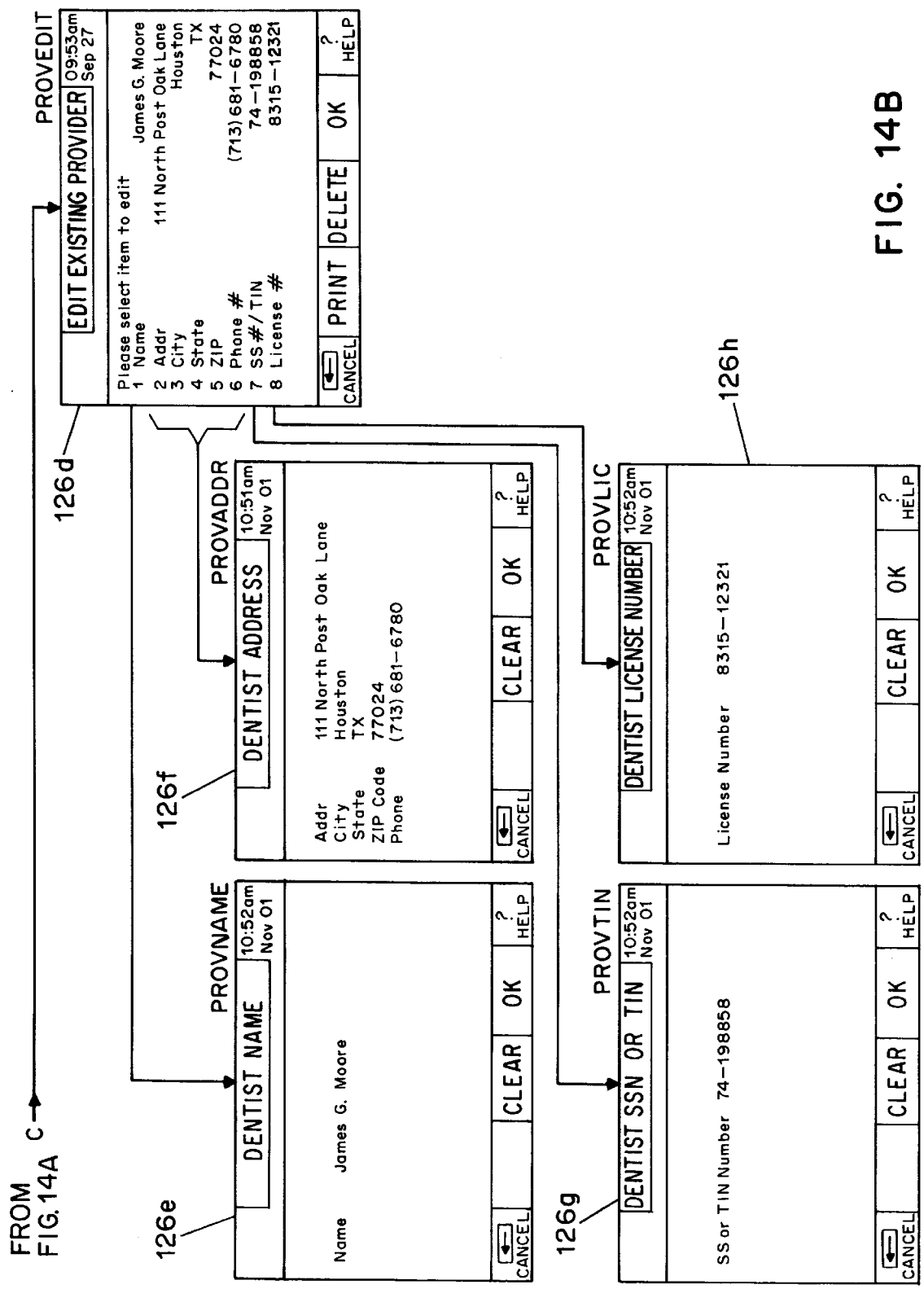
Figure 14C:
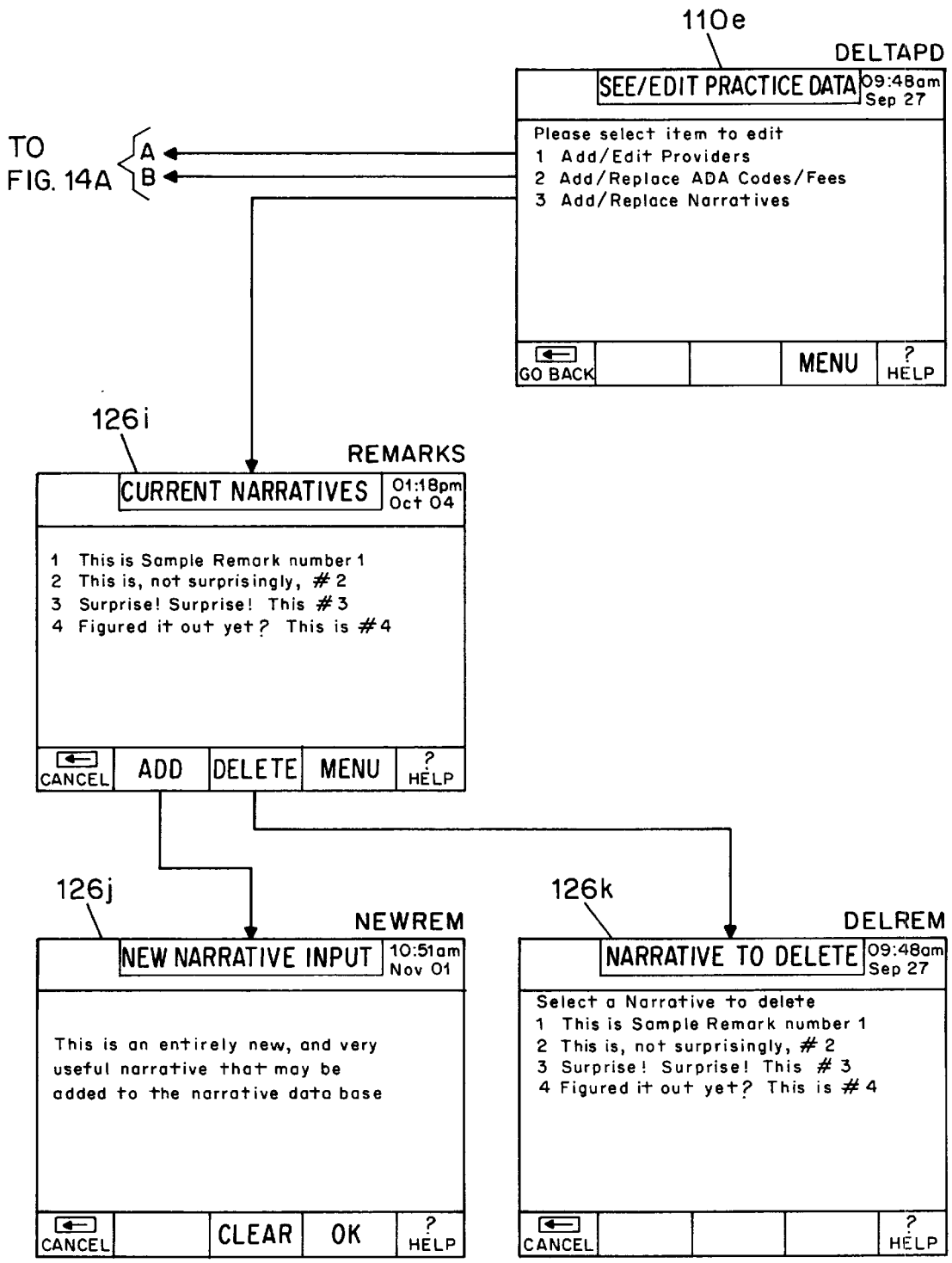

FIG. 14 illustrates a procedure, and the screens that may be displayed during this procedure, for editing various data files used in the claims assembling system. To initiate this procedure, the operator inputs "5" when page 2 of the Main Service Menu Screen is displayed on the monitor; and in response, screen 110e, shown in both FIGS. 8 and 11 is displayed on the screen 86.

With reference to FIG. 14, screen 110e lists three general categories of data files that can be changed: (1) Providers, (2) ADA codes, and (3) Narratives. Each of these data files is identified by a respective number on screen 110e, and to access one of these data files, the operator inputs the associated number.

Screens 126a–126h show the subroutine for changing data relating to the providers of the health care services; and this subroutine allows the operator to add names, to delete names, and to change data about listed providers. To add a name to the list of providers, the operator inputs a command signal, when screen 126a is shown, to display screen 126b; and then when this latter screen is shown, the operator simply enters the name of the provider that is to be added to the list. Analogously, to delete a name from the list of providers, the operator inputs a command signal, again when screen 126a is shown, to display screen 126c; and when this latter screen is shown, the operator deletes the name of the provider that is to be removed from the list.

Each provider listed on screen 126a is designated by a number; and to change data on file about a particular provider, the operator inputs the identifying number for that provider. In response, a screen, such as screen 126d, is shown displaying the data file for the provider. This screen contains four general types of data items: name, address, social security number or TIN, and license number. To change any of these data items, the operator inputs a respective command signal and in response, the screens 126e, 126f, 126g and 126h are respectively shown. When these latter four screens are shown, the operator makes the desired change to the information shown on the screens.

The routine of FIG. 14, may also be used to change the narratives on file. To do this, the operator inputs "3"when screen 110e is shown, and this causes screen 126i to be displayed. This screen lists the current narratives. To add a narrative, the operator inputs a command to show screen 126*j*, and then adds a new narrative to the screen. Statements may be added to the Narrative to Delete file; and to do this, the operator, when screen 126*i* is shown, inputs a command to show screen 126*k*, and the operator then adds a statement to the list of statements shown on this latter screen.

Figure 15:
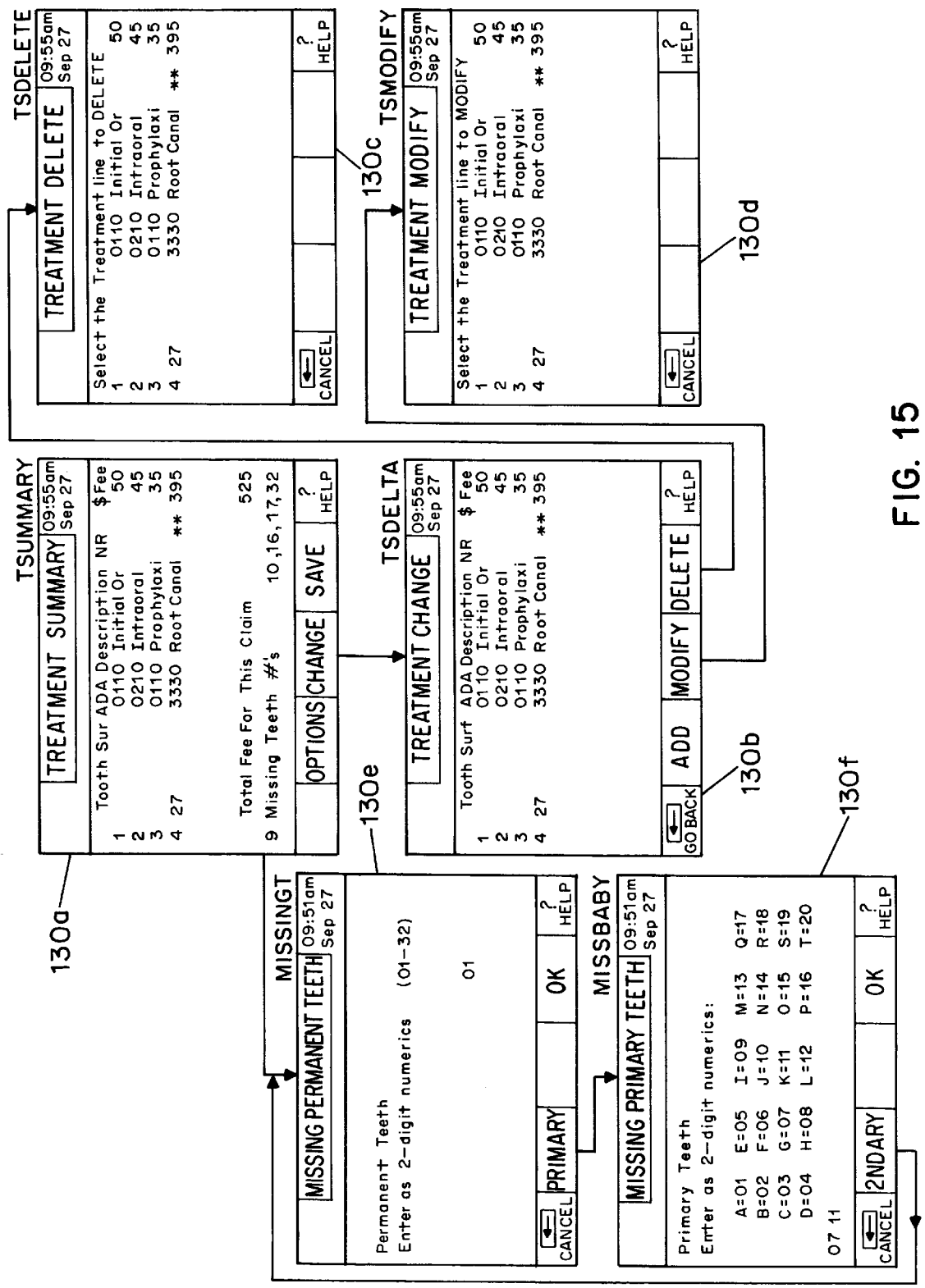
FIG. 15 illustrates a screen that presents a summary of certain treatment related data, and other screens that may be used to help change that treatment related data.

FIG. 15 illustrates a routine for displaying and changing a summary of the treatment services received by the patient. To start this routine, the operator inputs a command to show screen 130*a*, which illustrates that summary. If the operator wants to delete or modify data on this summary, the operator inputs a command to show screen 130*b*, and then the operator inputs a command to show either screen 130*c* or screen 130*d*. To delete an item from the list of items shown in the treatment summary screen 130*a*, the operator deletes that item from screen 130*c*; and to modify any of these items, the operator makes the desired changes to the information shown on screen 130*d*.

The routine illustrated in FIG. 15 may also be used to display and change selected patient specific data. In this example, screen 130*a* identifies any of the patient's teeth that are missing. If the operator wants to change this data, the operator inputs a command to show screen 130*e*. If the patient is missing any permanent teeth, a number identifying the tooth is entered. If the patient is missing primary teeth, the operator inputs a command to show screen 130*f*, and then enters a number identifying the missing tooth or teeth.

Figure 16A:
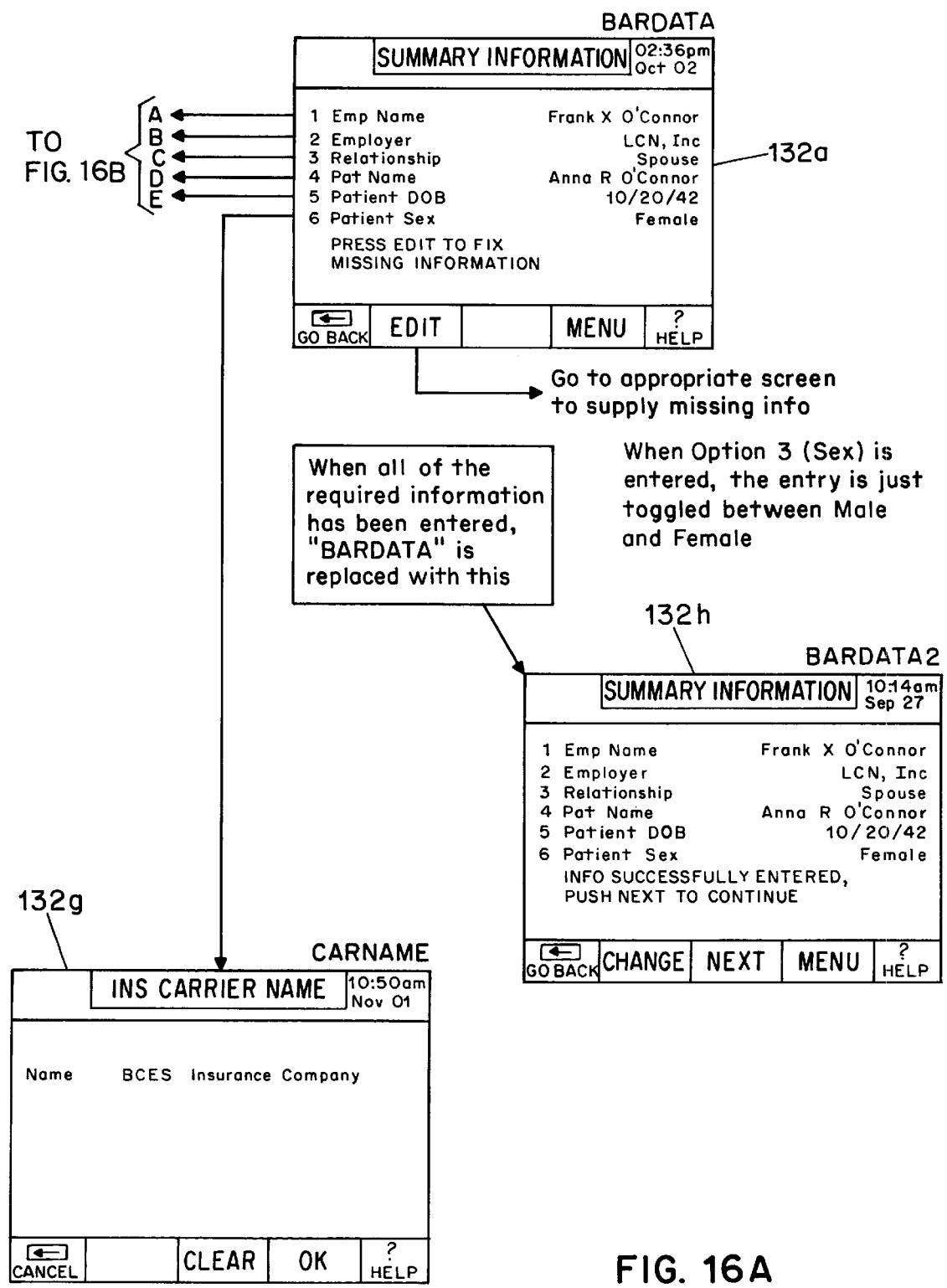
FIG. 16 shows a screen having a summary of some information on a patient's personal data file, and other screens that may be used to change that patient data.
Figure 16B:
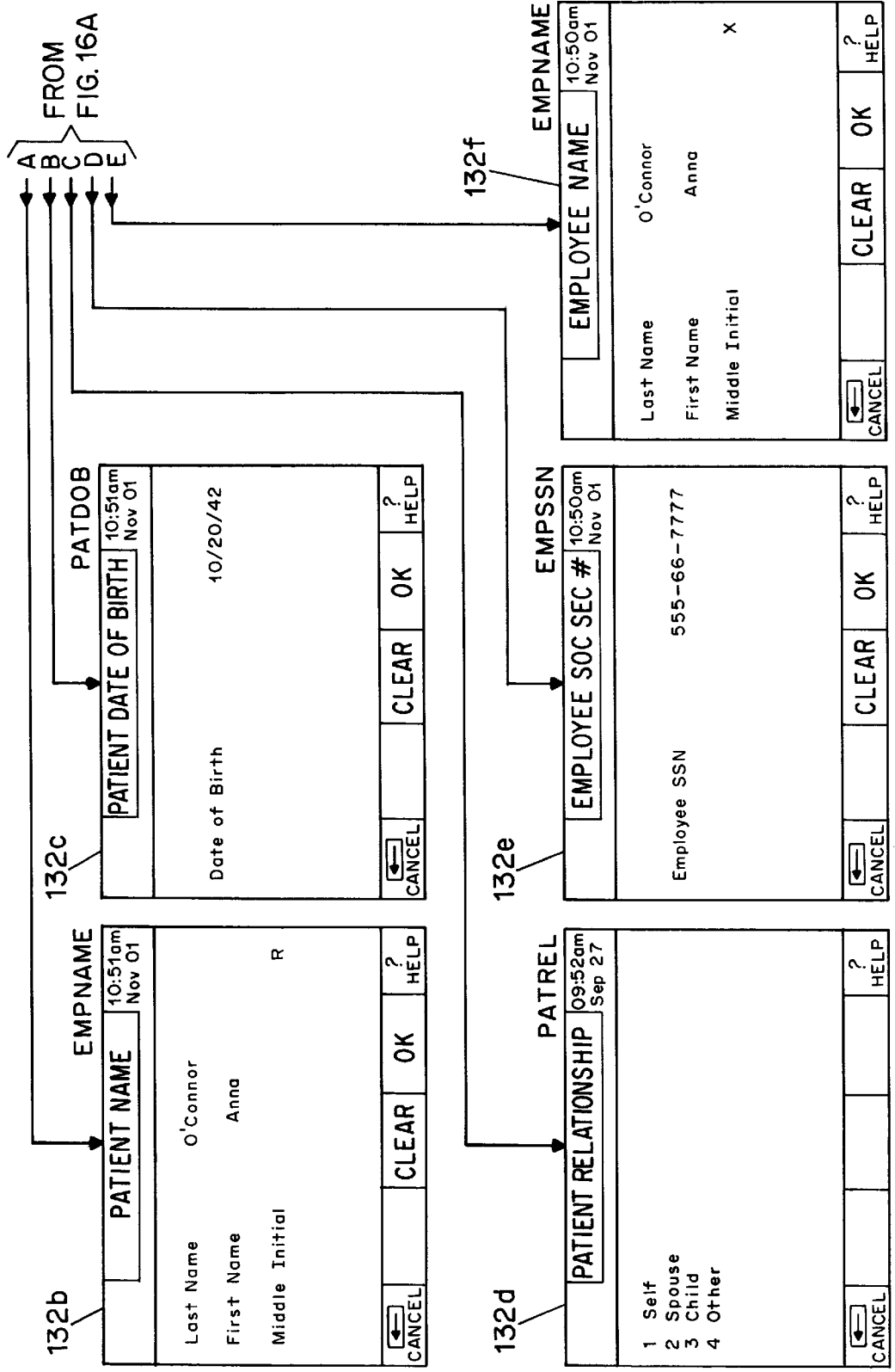

FIG. 16 shows a routine for displaying, and if desired, changing or adding to, selected personal data obtained from the patient's personal data file 20. To display this data, the operator inputs a command to show screen 132*a*. This screen lists the name of the participating employee, the employer, the relationship of the patient to that employee, and the patient's name and date of birth, and the name of the insurance carrier. Each of these data items is identified by a particular number. To change any of this data, the operator inputs the number of the data item to be changed; and in response, a respective one of the screens 132*b*–132*g* is shown. To change any of the data shown on screens 132*b*, 132*c*, 132*d*, 132*e*, 132*f* and 132*g*, the operator makes the change to the data shown on those screens. To change the description of the relationship between the patient and the participating employee, the operator selects the description from the group of descriptions given on screen 132*c*.

After all of the new or corrected data have been input, the operator inputs a signal to indicate that this has been done. In response, screen 132*h*, showing the entered data, is displayed on the video monitor.

Figure 17:
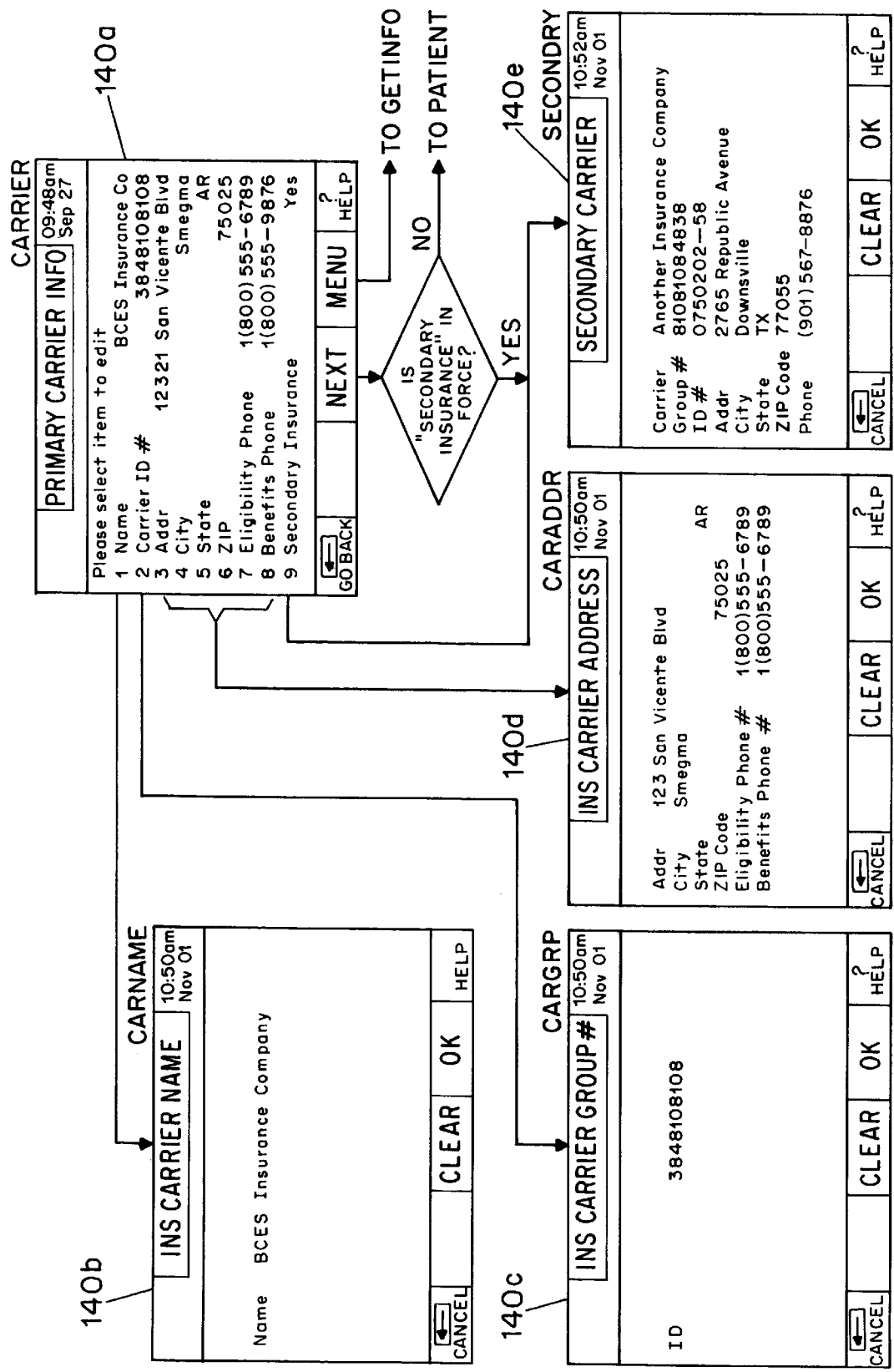
FIG. 17 illustrates a screen showing selected insurance data and additional screens that may be used to change that insurance data.

FIG. 17 shows a routine for displaying, and if desired changing or adding to, selected data obtained from the patient's personal data file describing the primary insurance carrier and any secondary insurance carrier. To start this routine, the operator inputs a signal to show screen 140*a* on the screen. This screen displays various data items about the primary insurance carrier, and whether the patient has a secondary insurance carrier. The data about the primary insurance carrier is separated into three groups or files: the insurance carrier's name, its group number, and its address. To change any of this data, the operator inputs a signal to display screens 140*b*, 140*c* or 140*d* respectively, and the operator then enters the appropriate change or changes.

If the patient has a secondary insurance carrier, data about this insurance carrier can be displayed by showing screen 140*e*, and any appropriate command may be used to have this screen shown on the video monitor. The operator, if he or she chooses, can then also change the data shown on screen 140*e*.

Figure 18:
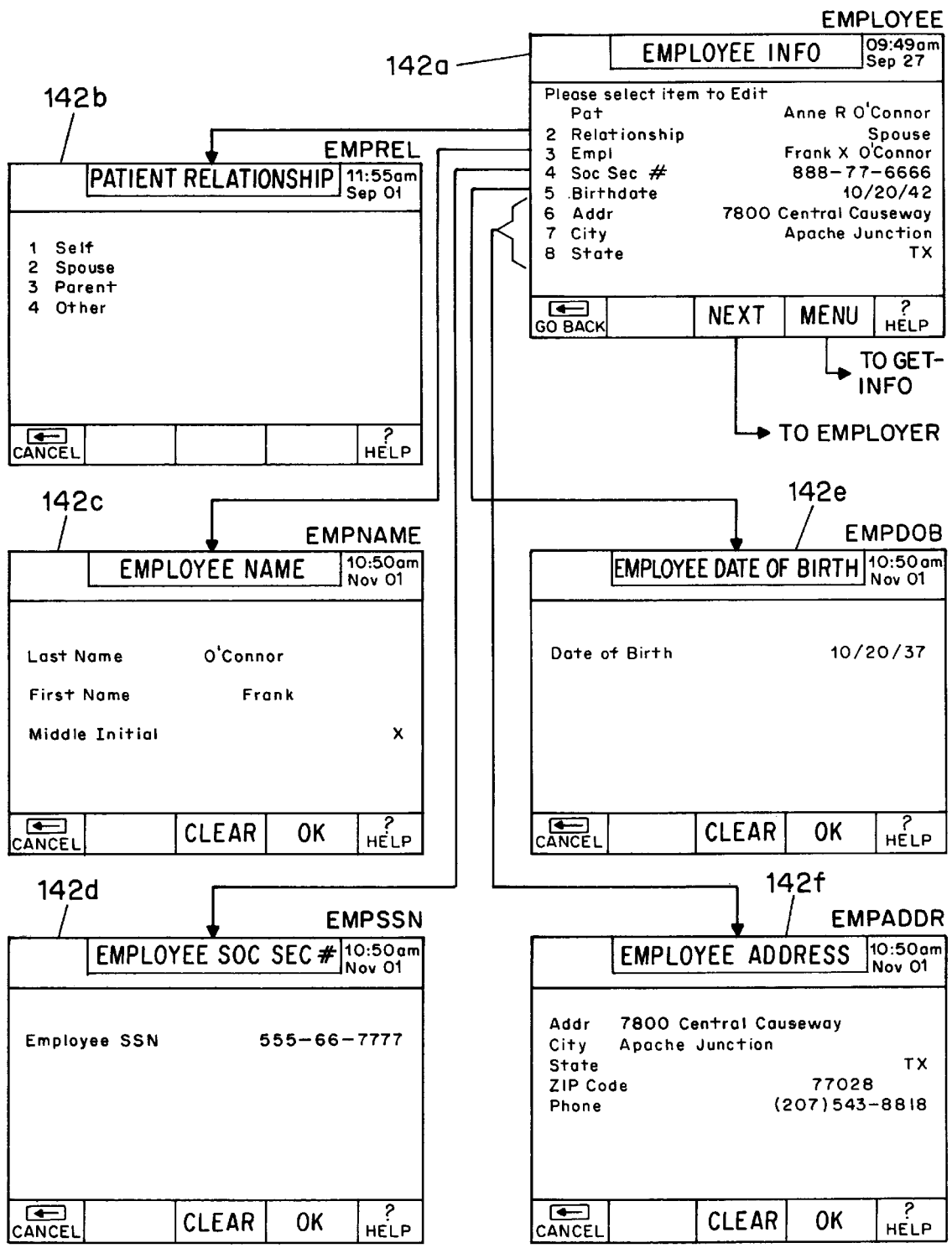
FIGS. 18, 19 and 20 illustrate screens showing data that may be used to assemble a health care claim, and other screens that may be used to help an operator change that data.
Figure 19A:
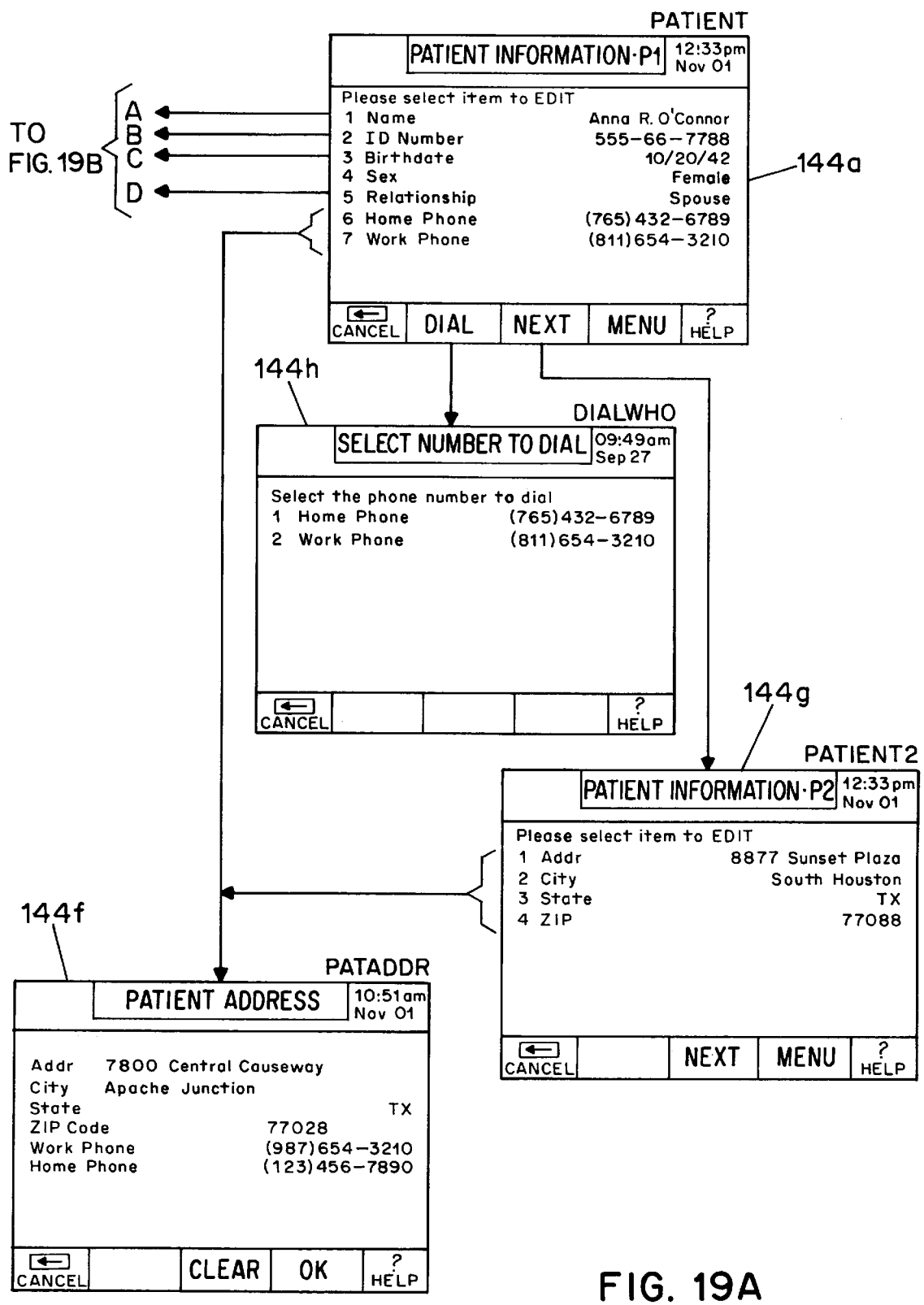
Figure 20:
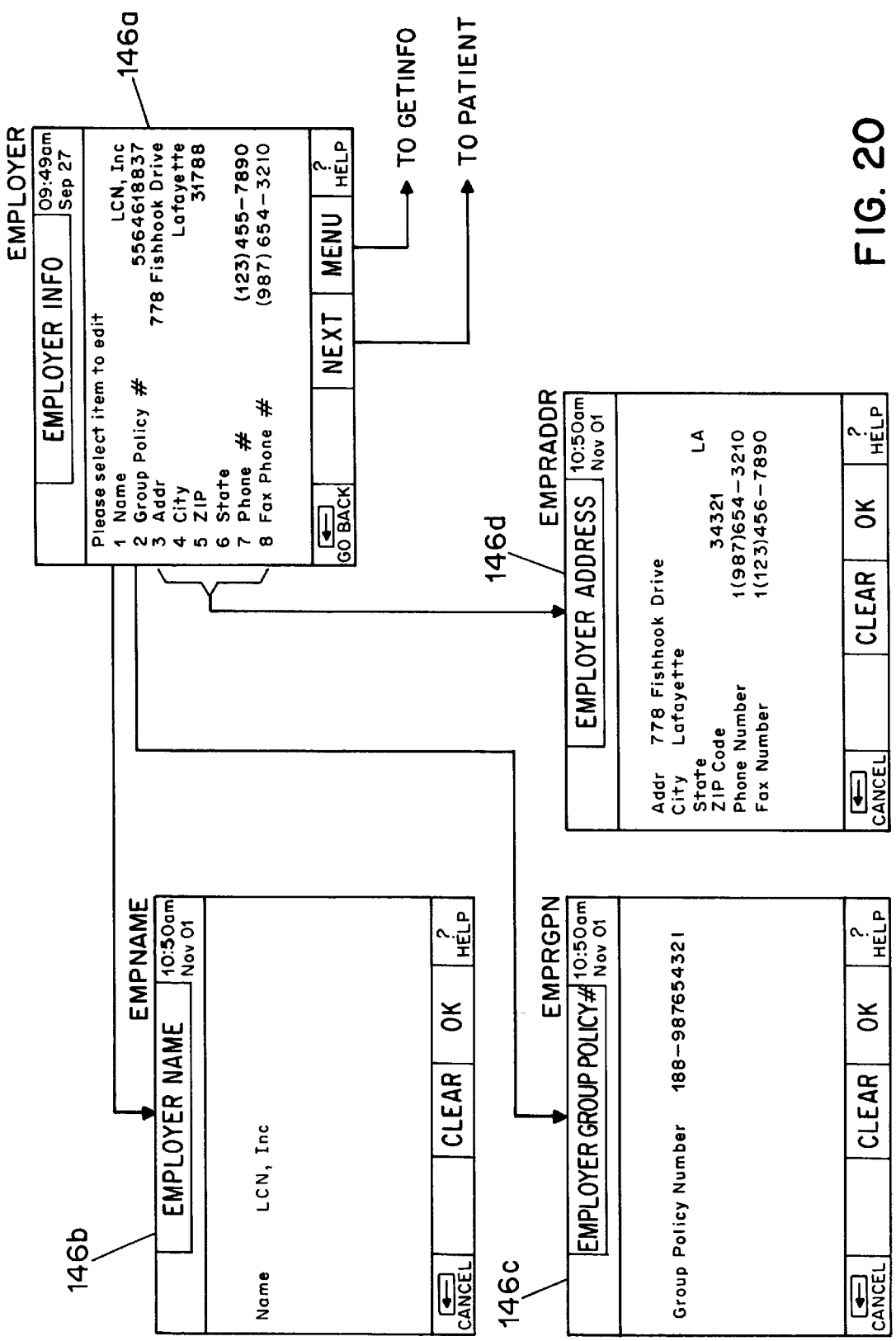

FIGS. 18, 19 and 20 show routines that may be used to display and change information about the employee, the patient, and the employer. In each of these routines, an initial screen may be shown displaying the relevant data, and the data on each of those screens can be changed by accessing other screens and then making the change or changes on those other screens.

With reference to FIG. 18, screen 142*a* shows selected information about the employee; and in particular, this screen shows the employee's name, his or her relationship to the patient, the employee's social security number, the employee's date of birth, and the employee's home address. To change any of this data, screens 142*b*–142*f* are accessed, and the desired change or changes are made to the data shown on those screens.

Screen 144*a* of FIG. 19 shows the patient's name, an identification number, birth date, sex, relationship to the insured, and home and work phone numbers. To change various of these data items, screens 144*b*–144*f* are accessed and the appropriate changes are made. With this example, the pertinent patient data can not all be shown on one screen, and thus the patient information screen has a second page 144*g*, which shows the patient's address. Changes to any of this data are also made via screen 144*f*. In addition, with the routine illustrated in FIG. 18, a screen 144*h* can be access from screen 144*a*, showing the preferred telephone number to use to contact the patient.

Screen 146*a* of FIG. 20 shows the employer's name, group policy number, and address and phone numbers. To change the employer's name, screen 146*b* is accessed; to change the employer's group policy number, screen 140*c* is accessed; and to change the address and phone numbers, screen 146*d* is accessed.

FIG. 21 shows a receipt 150 that will be retained by the doctor's office upon the filing of a health care claim. This preferred receipt 150 contains a significant amount of information that is useful for several reasons. The receipt provides important information about the services received by the patient and about the patient, and this receipt has important information about the filed health care claim, and thus is very useful in tracking that claim in the event of slow or non-payment.

More specifically, at 150*a*, the receipt shows the date that the claim was filed; at 150*b*, the receipt shows the patient's name and social security number and the claim number; and at 150*c*, the receipt shows the name of the individual, such as the doctor or dentist, who provided the treatment or services. The patient's personal data file is printed on the receipt at 150*d*, a description of the treatment or services is given at 150*e*, and the total fee is shown at 150*f*. Area 150*g* of the receipt is provided for collection remarks and information.

While it is apparent that the invention herein disclosed is well calculated to fulfill the objects previously stated, it will be appreciated that numerous modifications and embodiments may be devised by those skilled in the art, and it is intended that the appended claims cover all such modifications and embodiments as fall within the true spirit and scope of the present invention.

We claim:

1. A system for filing health care claims electronically when health care services are provided to a patient by a service provider and paid or recorded by a third party payor upon the receipt of a health care claim, said system comprising:

(a) a personal data card to be carried by the patient, said card bearing human readable indicia identifying the patient, and a machine readable data file, said data file including a two dimensional pattern of marks wherein the encoded marks together include a plurality of information words, including patient identification, third party insurer identification, and entitlement and benefit information relation to the relationship between the patient and the third party payor;

(b) a reader for scanning the machine readable data file and decoding said two dimensional pattern of marks into a plurality of separated patient digital fields and insurer digital fields, each of said fields enabling one or more information words to be decoded therefrom;

(c) means for entering a plurality of service provider digital fields entered by said service provider, said service provider digital fields representing service provided to said patient, (d) a data processing means for receiving said separated patient digital fields and said insurer digital fields from said reader, and said plurality of service provider digital fields entered by said service provider, said data processing means assembling said fields to form a health care claim to be presented to said payor for payment thereof on behalf of the patient;

(e) data memory means for storing one or more health care insurance claims for services rendered to one or more patients by said service provider as digital claims;

(f) data communication means for transmitting one or more of the digital claims from said service provider to said payor or clearing house via a common carrier.

2. A system for filing health care claims electronically as claimed in claim 1, wherein said means for entering a plurality of service provider digital fields includes a keyboard.

3. A system for filing health care claims electronically as claimed in claim 1, wherein said means for entering a plurality of service provider digital fields includes a Graphical User Interface and a touchscreen.

4. A system for filing health care claims electronically as claimed in claim 3, wherein said means for entering a plurality of service provider digital fields also includes a keyboard.

5. A system for filing health care claims electronically as claimed in claim 1, wherein said reader includes a scanner for scanning said two dimensional pattern of marks and generating a scan signal, and a decoder for converting said scan signal into said separate patient digital fields and converting said information words into ASCII characters within said fields.

6. A system for filing health care claims electronically as claimed in claim 4, wherein said system further includes a smart telephone, said telephone including said touchscreen, said keyboard, said data processing means, said data memory means and a modem for converting said digital claims into modulated signals for telephone transmission to said insurer or payor.

7. A system for filing health care claims electronically as claimed in claim 1, wherein said system further includes a common digital claim format to enable multiple claims to different payors to be filed with a medical claims clearing house in a single data transmission.

8. A system for filing health care claims electronically as claimed in claim 1, wherein said system further includes a printer for printing copies of said machine readable data file on a removable label that may be attached to a patient file maintained by said service provider for said patient.

9. A system as claimed in claim 1, further comprising: means for refiling or correcting and refiling a health care transaction by scanning the machine readable code produced by the printer at the time of the original electronic filing.

10. A system as claimed in claim 1, further comprising: means for providing health care facilities with electronic patient and other data by downloading an electronically printed bar code after receiving from the provider the minimal identification data of the policy holder.

11. A system as claimed in claim 1, further comprising: means for transferring data entered into the telecommunications device into a personal computer to populate the personal computer practice management system.

12. A system for filing health care claims electronically as claimed in claim 1, wherein said data file includes a telephone number for said payor encoded therein to enable said data processing means and said data communication means to automatically connect the service provider with the payor via a common carrier to verify a benefit or entitlement prior to providing service to said patient.

13. A health care data card for completing health care claims to be filed electronically when health care services are provided to a patient by a service provider and paid by a third party payor upon the receipt of a health care claim, said data card comprising a health care data card issued by the third party insurer and carried by the patient, said card bearing human readable indicia identifying the patient, the service provider, and a machine readable data file, said data file including at least two adjacent codewords, each codeword represented by a pattern of marks wherein the codewords together include a plurality of information words, including encoded patient identification fields, encoded third party insurer identification fields, and encoded fields denominating entitlement and benefit information representative of the relationship between the patient and the third party insurer, said card used by the service provider to verify benefits and entitlement prior to service, and to complete a health care claim for submission to said third party payor after the provision of health care benefits.

14. A health care data card for completing health care claims to be filed electronically as claimed in claim 13 wherein said machine readable data file is encoded in a two dimensional bar code format.

15. A health care data card for completing health care claims to be filed electronically as claimed in claim 13 wherein said machine readable data file is encoded in a PDF417 format.

16. A health care data card for completing health care claims to be filed electronically as claimed in claim 13 wherein said machine readable data file encodes said patient identification fields and said third party insurer identification fields in a standard field format to enable said service provider to electronically file multiple claims from different data cards issued by different insurers with a health care claims clearing house in a single data transmission.

17. A method of filing health care claims electronically when health care services are provided to a patient by a service provider and paid by a third party payor upon the receipt of a medical claim pursuant to a health care insurance policy, said method comprising:

(a) encoding a health care data card with a machine readable data file, said data file including a two dimensional pattern of marks wherein the encoded marks together include a plurality of information words, including patient identification, third party payor identification, and entitlement and benefit information relation to the relationship between the patient and the payor;

(b) imprinting the card with human readable indicia and issuing the card to a patient to be carried by the patient for a period as defined by said insurance policy, (c) scanning the machine readable data file at a service provider facility and decoding said two dimensional pattern of marks into a plurality of separated patient digital fields and insurer digital fields, each of said fields enabling one or more information words to be decoded therefrom;

(d) entering a plurality of service provider digital fields at said service provider facility, said service provider digital fields representing at least one service provided to said patient, (e) interleaving said separated patient digital fields and said insurer digital fields from said scanning step and said plurality of service provider digital fields from said entering step and assembling said fields electronically to form a health care claim to be presented to said payor for payment thereof on behalf of the patient;

(f) assembling one or more health care claims for services rendered to one or more patients by said service provider; and (g) electronically transmitting said health care claim(s) for services rendered to said patients(s) by said service provider to said insurer via a common carrier data communication.

18. An apparatus for filing health care claims electronically when health care services are provided to a patient by a service provider and paid by a third party payor upon the receipt of a medical claim pursuant to a health care policy, said apparatus comprising:

(a) a scanner for scanning a machine readable data file encoded on a health care data card carried by the patient, said data file including a two dimensional pattern of marks wherein the encoded marks together include a plurality of information words, including patient identification, third party payor identification, and entitlement and benefit information relation to the relationship between the patient and the third party payor;

(b) a decoding means for decoding said two dimensional pattern of marks into a plurality of separated patient digital fields and payor digital fields, each of said fields enabling one or more information words to be decoded therefrom;

(c) data entry means for entering a plurality of service provider digital fields entered by said service provider, said service provider digital fields representing service provided to said patient, (d) a data processing means for receiving said separated patient digital fields and said insurer digital fields from said reader, and said plurality of service provider digital fields entered by said service provider, said data processing means assembling said fields to form a health care claim to be presented to said payor for payment thereof on behalf of the patient;

(e) data memory means for storing one or more health care claims for services rendered to one or more patients by said service provider;

(f) data communication means for transmitting one or more health care claims from said service provider to said payor via a common carrier.

19. A system for assembling, filing and processing health care claims made by patients pursuant to coverage policies issued to the patients by claim payors for service provided to the patients at health care facilities, the network comprising:

a multitude of participating patients, each of the patients having a respective one portable personal data file including a set of patient related data including patient identification, third party payor identification, and entitlement and benefit information relation to the relationship between the patient and the payor and encoded in a machine readable format;

a multitude of health care facilities, for providing health care services to the participating patients, each of the health care facilities having i) a telecommunications unit, and ii) a file reader to read the data on the personal data files and to transmit the patient related data to the telecommunications unit at the facility, wherein the telecommunications unit includes a control program having (1) a series of prompts, and (2) a claim assembling program to present the prompts in a human understandable format to solicit from an operator data related to services provided to the patients at the health care facility, and to assemble the patient related data from the personal data files and the service related data from the operator into electronic claim forms;

a plurality of claim payor companies having telecommunications units;

a central clearinghouse connected to the telecommunications units of the health care facilities and connected to the telecommunications units of the claim payor companies, the claims processing unit including means to receive the electronic claim forms from the health care facilities, to check the electronic claim forms and to transmit said claims to the payor companies for adjudication and payment.

20. A system according to claim 19, wherein each electronic claim form is prepared for an associated service received by one of the patients, and each electronic claim form is prepared at and when the associated service is received by said one of the patients.

21. A computer system for electronically assembling a health insurance claim, each of said claims including patient related data and treatment related data, the system comprising:

a data processing unit;

a memory unit including a claim assembly area;

means connecting the clearinghouse unit and the memory unit together to transmit data therebetween;

input means for receiving data, and including i) means to receive patient related data including patient identification, third party payor identification, and entitlement and benefit information relation to the relationship between the patient and the payor in an electronic format, and ii) means to receive input from an operator;

output means for transmitting data from the computer system, and including a screen; and a control program stored in the data processing unit, and including i) a series of prompts, and ii) a claim assembling program to present the prompts on the screen in a predefined order to prompt the operator to input the treatment related data, and to transmit the patient related data and the treatment related data to the claim assembly area to assemble an electronic claim form therein.

22. A computer system according to claim 21, wherein:

the control program further includes a series of data files, identifying possible responses to the prompts; and the claim assembly program further includes i) means to display the data files on the screen to help the operator respond to the prompt, and ii) means to access the data files to change the possible responses identified therein.

23. A computer program for electronically assembling health care claims in a computer system, wherein each of the health care claims includes patient related data and treatment related data, and wherein the program is for use with a computer system including a data processing unit, a memory unit, first input means to receive patient related data in an electronic format, second input means to receive input from an operator, and a screen, the computer program comprising:

a carrier medium; and a control program stored on the carrier medium, and including i) a series of prompts, and ii) a claim assembling program for operating the computer system to present the prompts on the video monitor in a predefined order to prompt the operator to input the treatment related data, and to transmit the patient related data including patient identification, third party payor identification, and entitlement and benefit information relation to the relationship between the patient and the payor and the treatment related data to the memory area of the computer system to assemble an electronic claim form in said memory area.

24. A computer program according to claim 23, wherein:

the control program further includes a series of data files for holding possible responses to the prompts; and the claim assembling program is adapted to operate the computer system to display the data files on the screen to help the operator respond to the prompts, and to access the data files to change the possible responses held therein.

25. A system for processing insurance claims for services received by patients, the system comprising:

a portable personal data file including a set of data related to a patient including patient identification, third party payor identification, and entitlement and benefit information relation to the relationship between the patient and the payor and encoded in a machine readable format;

a local telecommunications unit including i) input means for receiving input data from an operator, ii) output means, iii) a memory unit, iv) a control program, and v) a series of prompts stored in the memory area for soliciting input data from the operator related to services received by the patient; and a reader for reading the patient related data from the portable personal data file and transmitting said patient related data to the processing unit;

wherein the control program operates (i) to present the prompts on the output means in a human understandable format and in an order determined in accordance with a preset program, to solicit from the operator the treatment related data, and (ii) to assemble the patient related data received from the reader and the treatment related data received from the operator, in the memory area to form an electronic claim form therein.

26. A system according to claim 25, wherein each claim is made pursuant to a coverage policy, and the system further comprises:

a central claims processing unit;

means to transmit the electronic claim form from the local telecommunications unit to the central claims processing unit;

the central processing unit further includes means to adjudicate the electronic claim form in accordance with the coverage policy to determine a response to the claim.

27. A system according to claim 26, wherein the means to transmit the electronic claim form includes:

a common carrier of electronic data;

a modem connected to the local telecommunications unit and the common carriers for receiving the electronic claim form from the local processing unit and converting the electronic claim form into a format suitable for transmission over the common carrier.

28. A method for processing insurance claims for services received by patients, the method comprising:

providing a two-dimensional portable personal data file including a set of data related to a patient including patient identification, third party payor identification, and entitlement and benefit information relation to the relationship between the patient and the payor and encoded in a machine readable format;

providing a local telecommunications unit including a memory section;

using a machine to read the patient related data from the portable personal data file and to transmit said patient related data to the telecommunications unit;

presenting a series of prompts to an operator, in an order determined in accordance with a preset program, to solicit from the operator input data related to services received by the patient;

responding to the prompts by inputting to the telecommunications unit the service related data; and assembling the patient related data and the treatment related data in the memory section of the telecommunications unit to form an electronic claim form therein.

29. A method according to claim 28, further including the steps of:

providing a central claims clearinghouse unit to forward the electronic claim form to the correct insurance company;

transmitting the electronic claim form from the local telecommunications unit to the central claims processing unit; and operating the central claim processing unit to adjudicate the electronic claim form, and to determine a response thereto.

* * * * *